US010420468B2

(12) United States Patent
Takahashi et al.

(10) Patent No.: US 10,420,468 B2
(45) Date of Patent: Sep. 24, 2019

(54) INFORMATION PROCESSING APPARATUS, SURGERY MICROSCOPE SYSTEM, AND INFORMATION PROCESSING METHOD

(71) Applicant: SONY CORPORATION, Tokyo (JP)

(72) Inventors: Yoshitomo Takahashi, Kanagawa (JP); Tomoyuki Ootsuki, Kanagawa (JP); Tatsumi Sakaguchi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 66 days.

(21) Appl. No.: 15/532,074

(22) PCT Filed: Dec. 2, 2015

(86) PCT No.: PCT/JP2015/005995
§ 371 (c)(1),
(2) Date: May 31, 2017

(87) PCT Pub. No.: WO2016/098300
PCT Pub. Date: Jun. 23, 2016

(65) Prior Publication Data
US 2017/0273559 A1 Sep. 28, 2017

(30) Foreign Application Priority Data
Dec. 18, 2014 (JP) .................. 2014-256040

(51) Int. Cl.
*A61B 3/00* (2006.01)
*A61B 3/15* (2006.01)
(Continued)

(52) U.S. Cl.
CPC .............. *A61B 3/15* (2013.01); *A61B 3/0025* (2013.01); *A61B 3/1005* (2013.01); *A61B 3/13* (2013.01);
(Continued)

(58) Field of Classification Search
CPC ............ A61B 34/00; A61B 3/00; G02B 21/00
(Continued)

(56) References Cited

U.S. PATENT DOCUMENTS 9,182,816 B2 * 11/2015 Kasahara ............... G06F 3/0487
2006/0247659 A1 * 11/2006 Moeller ................. A61B 3/107
606/107
2011/0230751 A1 * 9/2011 Kersting ............. A61F 9/00736
600/407

FOREIGN PATENT DOCUMENTS

CH 699725 B1 4/2010
CH 700502 B1 9/2010
(Continued)

OTHER PUBLICATIONS

International Search Report and Written Opinion of PCT Application No. PCT/JP2015/005995, dated Mar. 1, 2016, 01 pages of English Translation and 08 pages of ISRWO.

*Primary Examiner* — Abolfazl Tabatabai
(74) *Attorney, Agent, or Firm* — Chip Law Group

(57) ABSTRACT

[Object] To provide an information processing apparatus that is capable of presenting navigation information for ophthalmic surgery at high speed and with high precision. [Solving Means] An information processing apparatus according to the present technology includes a magnification acquisition unit and an image generation unit. The magnification acquisition unit acquires a magnification of a target image with respect to a reference image, the reference image being an image of an eye to be treated, the target image being an image of the eye picked up at a time different from an imaging time of the reference image. The image generation unit generates a navigation image including navigation information for guiding treatment of the eye on the basis of the magnification acquired by the magnification acquisition unit.

14 Claims, 25 Drawing Sheets

(51) Int. Cl.

| | | |
|---|---|---|
| *A61F 9/007* | (2006.01) | |
| *A61B 90/20* | (2016.01) | |
| *A61B 3/10* | (2006.01) | |
| *A61B 3/13* | (2006.01) | |
| *A61B 34/00* | (2016.01) | |
| *A61B 90/00* | (2016.01) | |
| *A61B 34/20* | (2016.01) | |
| *G02B 21/00* | (2006.01) | |
| *G06K 9/00* | (2006.01) | |
| *G02B 21/36* | (2006.01) | |
| *A61B 3/11* | (2006.01) | |

(52) U.S. Cl.
CPC .............. *A61B 34/20* (2016.02); *A61B 34/25* (2016.02); *A61B 90/20* (2016.02); *A61B 90/36* (2016.02); *A61F 9/007* (2013.01); *G02B 21/0012* (2013.01); *A61B 3/112* (2013.01); *A61B 2034/2055* (2016.02); *A61B 2034/2065* (2016.02); *A61B 2034/254* (2016.02); *A61B 2090/364* (2016.02); *A61B 2090/365* (2016.02); *G02B 21/365* (2013.01); *G02B 21/367* (2013.01)

(58) Field of Classification Search
USPC .................................................. 382/100, 117
See application file for complete search history.

(56) References Cited

FOREIGN PATENT DOCUMENTS

| | | |
|---|---|---|
| CN | 102264280 A | 11/2011 |
| DE | 102004055683 A1 | 5/2006 |
| EP | 2184005 A1 | 5/2010 |
| JP | 2006-136714 A | 6/2006 |
| JP | 2012-506272 A | 3/2012 |
| JP | 2014-121643 A | 7/2014 |
| WO | 2010/046371 A1 | 4/2010 |

\* cited by examiner

INFORMATION PROCESSING APPARATUS, SURGERY MICROSCOPE SYSTEM, AND INFORMATION PROCESSING METHOD

CROSS REFERENCE TO RELATED APPLICATIONS

This application is a U.S. National Phase of International Patent Application No. PCT/JP2015/005995 filed on Dec. 2, 2015, which claims priority benefit of Japanese Patent Application No. JP 2014-256040 filed in the Japan Patent Office on Dec. 18, 2014. Each of the above-referenced applications is hereby incorporated herein by reference in its entirety.

TECHNICAL FIELD

The present technology relates to an information processing apparatus, a surgery microscope system, and an information processing method that guide ophthalmic surgery.

BACKGROUND ART

A treatment guide apparatus used in ophthalmic surgery and the like superimposes navigation information on an image of an eye to be treated, and presents it to a practitioner (see, for example, Patent Literature 1). The navigation information is, for example, information indicating an insertion position of a surgical tool or an insertion position of an intraocular lens. Specifically, the treatment guide apparatus presents an image of an eye picked up by an examination apparatus before surgery (hereinafter, referred to as examination image) to a practitioner. The practitioner refers to the examination image to consider an insertion position of a surgical tool, an orientation of an intraocular lens, and the like, and specifies them as preoperative planning on the examination image.

The treatment guide apparatus compares an image of an eye to be treated picked up via a surgery microscope before starting surgery (hereinafter, referred to as the surgery image) with the examination image, and performs alignment (registration) of the images. After that, the treatment guide apparatus superimposes the preoperative planning specified on the examination image on the surgery image as navigation information, and presents it to the practitioner.

When treatment is started, the treatment guide apparatus tracks eye movement by tracking processing (alignment between consecutive frames or arbitrary frames), and updates the navigation information depending on the eye movement. The practitioner performs treatment while referring to the navigation information. Accordingly, it is possible to compensate for lack of experience or improve the safety of surgery, QoL (quality of life) after surgery, and the like.

CITATION LIST

Patent Literature

Patent Literature 1: Japanese Patent Application Laid-open No. 2014-121643

DISCLOSURE OF INVENTION

Technical Problem

As described above, the arrangement of the navigation information is determined on the basis of alignment between the examination image and the surgery image, alignment between surgery images, and the like. Note that rotation, a scale change, an illumination change, and the like may be caused in images. The treatment guide apparatus needs to update the navigation information at high speed and with high precision in response to such a change in the imaging condition. However, it is not easy to satisfy both of the processing speed and precision because computational complexity of the alignment processing is high.

In view of the circumstances as described above, it is an object of the present technology to provide an information processing apparatus that is capable of presenting navigation information for ophthalmic surgery at high speed and with high precision.

Solution to Problem

In order to achieve the above-mentioned object, an information processing apparatus according to an embodiment of the present technology includes a magnification acquisition unit and an image generation unit.

The magnification acquisition unit acquires a magnification of a target image with respect to a reference image, the reference image being an image of an eye to be treated, the target image being an image of the eye picked up at a time different from an imaging time of the reference image.

The image generation unit generates a navigation image including navigation information for guiding treatment of the eye on the basis of the magnification acquired by the magnification acquisition unit.

With this configuration, a navigation image including navigation information is generated on the basis of the magnification between a reference image and a target image. The magnification between the reference image and the target image is changed by the magnification of the imaging apparatus (surgery microscope, etc.) that picks up these images, the distance between the imaging apparatus and the eye, and the like. However, this information processing apparatus is capable of using the change in the magnification to generate a navigation image.

The magnification acquisition unit may acquire the magnification on the basis of a ratio between a size of an image of an object detected in the reference image and a size of an image of the object detected in the target image.

With this configuration, the magnification acquisition unit is capable of acquiring the magnification between the reference image and the target image by using the ratio of the size of an object (a cornea or a pupil of an eye, a marker made on an eye by a practitioner, or the like) included in the reference image and the target image.

The magnification acquisition unit may acquire the magnification on the basis of a ratio between a distance between an imaging apparatus and the eye of a time when the reference image is picked up and a distance between the imaging apparatus and the eye of a time when the target image is picked up.

With this configuration, the magnification acquisition unit is capable of acquiring the magnification between the reference image and the target image by using the distance between the imaging apparatus and the eye to be treated acquired from the imaging apparatus.

The magnification acquisition unit may acquire the magnification on the basis of a ratio between a zoom factor of an imaging apparatus of a time when the reference image is picked up and a zoom factor of the imaging apparatus of a time when the target image is picked up.

With this configuration, the magnification acquisition unit is capable of acquiring the magnification between the reference image and the target image by using the zoom factor of the imaging apparatus acquired from the imaging apparatus.

The magnification acquisition unit may acquire the magnification on the basis of a ratio between a distance between an imaging apparatus and the eye of a time when the reference image is picked up and a distance between the imaging apparatus and the eye of a time when the target image is picked up, and a ratio between a zoom factor of an imaging apparatus of the time when the reference image is picked up and a zoom factor of the imaging apparatus of the time when the target image is picked up.

With this configuration, the magnification acquisition unit is capable of acquiring the magnification between the reference image and the target image by using both of the distance between the imaging apparatus and the eye to be treated and the zoom factor of the imaging apparatus acquired from the imaging apparatus.

The image generation unit may perform image matching of the reference image and the target image by using the magnification, and generate the navigation image by using a result of the image matching.

The image matching can be performed at higher speed and with high precision if the magnification between the reference image and the target image to be matched is known in advance. With the above-mentioned configuration, the image generation unit is capable of performing image matching at high speed and with high precision by using the magnification acquired by the magnification acquisition unit.

The image generation unit may include a characteristic point detection unit that detects a characteristic point in each of the reference image and the target image, and the characteristic point detection unit may detect a characteristic point in the target image by using the magnification.

With this configuration, the characteristic point detection unit is capable of increasing the detection speed of the characteristic point detection in the target image by using the magnification that is known in advance.

The characteristic point detection unit may include a scale range determination unit and a DoG image generation unit, the scale range determination unit determining a scale range of a Gaussian filter for generating a smoothed image for each of the reference image and the target image, the DoG image generation unit generating a DoG image in a scale range determined by the scale range determination unit for each of the reference image and the target image, and the scale range determination unit may control a scale range for the target image by the magnification.

In SIFT (Scale-Invariant Feature Transform) that is an image matching method, because a standard deviation that gives the extreme value of a DoG (Difference of Gaussian) value can be estimated in the case where a scale (magnification) between images is known and it only needs to search for the extreme value of a DoG value in only a standard deviation value in a range close thereto as a search range, it is possible to reduce the computational complexity. Therefore, with the above-mentioned configuration, it is possible to increase the detection speed of the characteristic point detection, i.e., the speed of the image matching as compared with the case where a scale (magnification) between images is unknown.

The image generation unit may include a characteristic point matching unit that matches characteristic points detected in the reference image and the target image, and the characteristic point matching unit may perform the matching by using the magnification.

With this configuration, the characteristic point matching unit is capable of using the magnification that is known in advance to determine whether or not the pair of characteristic points of the reference image and the target image is right, and it is possible to improve the precision of the characteristic point matching.

The characteristic point matching unit may include a characteristic point pair selection unit and a scale value comparison unit, characteristic point pair selection unit selecting a characteristic point pair, the characteristic point pair being a pair of characteristic points detected in the reference image and the target image, the scale value comparison unit determining whether or not the characteristic point pair is right by using a scale ratio of the characteristic point pair, and the scale value comparison unit may control a scale ratio to be determined to be right by using the magnification.

In SIFT, a correlation value of the characteristic amount is used to make a pair of characteristic points detected in images to be compared, and thus, the characteristic point pair is generated. Note that the correlation value of the characteristic amount is disturbed due to the influence of noise in images, or the like, and the pair having the largest correlation value is not necessarily a right pair in some cases. With the above-mentioned configuration, the characteristic point matching unit is capable of determining whether or not the characteristic point pair is right by comparing the scale ratio of the characteristic point pair in addition to the correlation value of the characteristic amount, and it is possible to improve the precision of the characteristic point matching as compared with the case where a scale between images is unknown.

The image generation unit may include a characteristic point detection unit and a characteristic point matching unit, the characteristic point detection unit detecting a characteristic point in each of the reference image and the target image, the characteristic point matching unit matching characteristic points detected in the reference image and the target image, the characteristic point detection unit may detect a characteristic point in the target image by using the magnification, and the characteristic point matching unit may perform the matching by using the magnification.

As described above, the image generation unit is capable of increasing the speed of the characteristic point detection by using the magnification to detect the characteristic point, and improve the precision of the characteristic point matching by using the magnification for the characteristic point matching. Specifically, the image generation unit is capable of improving the speed and precision of the image matching by using the magnification.

The image generation unit may generate a navigation image including navigation information that is different depending on the magnification.

With this configuration, the information processing apparatus is capable of presenting suitable navigation information to a practitioner depending on the magnification.

The image generation unit may generate a navigation image including first navigation information when the magnification is less than a threshold value, and a navigation image including second navigation information when the magnification is not less than the threshold value, the first navigation information including a scale arranged at predetermined intervals, the second navigation information including a scale arranged at intervals smaller than those of the first navigation information.

With this configuration, the second navigation information having a scale arranged at small intervals is presented when a practitioner increases the magnification of the target image, and the second navigation information having a scale arranged at large intervals is presented when the practitioner decreases the magnification of the target image. Accordingly, navigation information having an appropriate scale is presented depending on the intention of a practitioner, and it is possible to improve the convenience of the practitioner.

In order to achieve the above-mentioned object, a surgery microscope system according to an embodiment of the present technology includes a surgery microscope and an information processing apparatus.

The surgery microscope picks up an image of an eye to be treated.

The information processing apparatus includes
  a magnification acquisition unit that acquires a magnification of a target image with respect to a reference image, the reference image being an image of the eye, the target image being an image of the eye picked up at a time different from an imaging time of the reference image, and
  an image generation unit that generates a navigation image for guiding treatment of the eye on the basis of the magnification acquired by the magnification acquisition unit.

In order to achieve the above-mentioned object, an information processing method according to an embodiment of the present technology includes acquiring, by a magnification acquisition unit, a magnification of a target image with respect to a reference image, the reference image being an image of an eye to be treated, the target image being an image of the eye picked up at a time different from an imaging time of the reference image.

By an image generation unit, a navigation image for guiding treatment of the eye is generated on the basis of the magnification acquired by the magnification acquisition unit.

Advantageous Effects of Invention

As described above, in accordance with the present technology, it is possible to provide an information processing apparatus that is capable of presenting navigation information for ophthalmic surgery at high speed and with high precision. It should be noted that the effect described here is not necessarily limitative and may be any effect described in the present disclosure.

MODE(S) FOR CARRYING OUT THE INVENTION (Overview of Ophthalmic Surgery)

Figure 1:
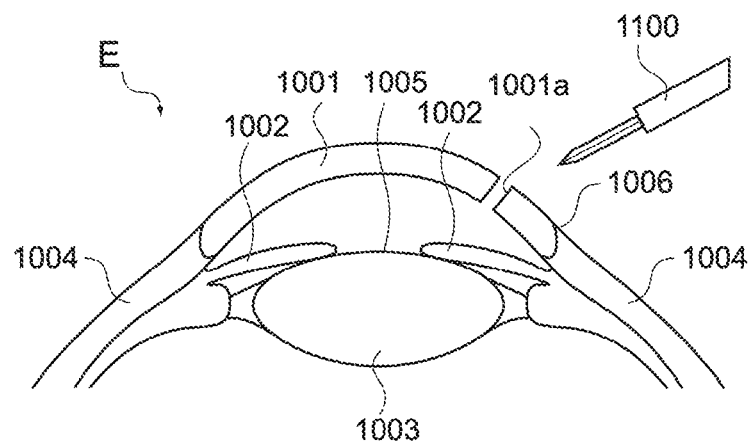
FIG. 1 A schematic diagram showing a process for ophthalmic surgery in which a surgery microscope system according to each embodiment of the present technology can be used.
Figure 2:
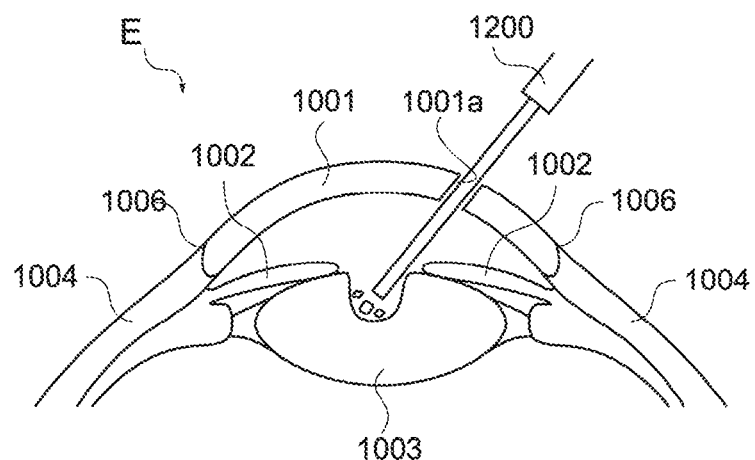
FIG. 2 A schematic diagram showing a process for ophthalmic surgery in which the surgery microscope system can be used.

An overview of ophthalmic surgery in which a surgery microscope system according to each embodiment of the present technology can be used will be described. FIG. 1 and FIG. 2 are each a schematic diagram showing a process for cataract surgery on an eye E to be treated. As shown in these figures, the eye E includes tissues such as a cornea 1001, an iris 1002, a lens 1003, and a sclera 1004. A pupil 1005 is in the iris 1002 on the surface of the lens 1003, and a corneal limbus 1006 is at the outer periphery of the cornea 1001.

As shown in FIG. 1, in cataract surgery, an incision 1001a is made by a surgical tool 1100 such as a knife. Next, as shown in FIG. 2, a surgical tool 1200 for suction is inserted from the incision 1001a, and the inside (nucleus or cortex) of the lens 1003 is sucked and removed. After that, an intraocular lens is inserted in the position where the lens 303 is removed, and thus, the surgery is completed.

Note that the cataract surgery described here is an example of the ophthalmic surgery in which the surgery microscope system according to each embodiment of the present technology can be used, and the surgery microscope system according to each embodiment of the present technology can be used in various kinds of ophthalmic surgery. Further, the surgery microscope system according to each embodiment of the present technology can be used also for surgery other than ophthalmic surgery.

First Embodiment

A surgery microscope system according to a first embodiment of the present technology will be described.

[Configuration of Surgery Microscope System]

Figure 3:
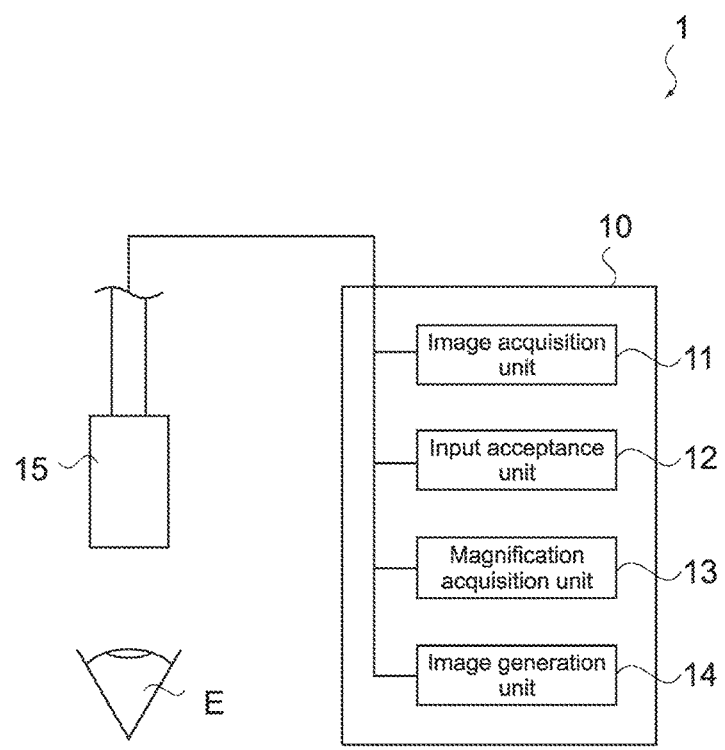
FIG. 3 A schematic diagram showing a configuration of a surgery microscope system according to a first embodiment of the present technology.

FIG. 3 is a block diagram showing a configuration of a surgery microscope system 1 according to this embodiment. As shown in the figure, the surgery microscope system 1 includes an information processing apparatus 10 and a surgery microscope 15.

The information processing apparatus 10 is an apparatus that is capable of performing information processing, such as a personal computer. The information processing apparatus 10 may be integrally formed with the surgery microscope 15, or may be an apparatus independent from the surgery microscope 15. The configuration of the information processing apparatus 10 will be described later.

As shown in FIG. 3, the surgery microscope 15 faces the eye E to be treated, and picks up a microscope magnified image of the eye E. The configuration of the surgery microscope 15 is not particularly limited as long as the surgery microscope 15 is capable of picking up an image of the eye E. The surgery microscope 15 is capable of optically or digitally changing the magnification of the image, or changing the magnification of the image also with a relative position (distance) between the surgery microscope 15 and the eye E.

[Configuration of Information Processing Apparatus]

As shown in FIG. 3, the information processing apparatus 10 includes an image acquisition unit 11, an input acceptance unit 12, a magnification acquisition unit 13, and an image generation unit 14.

The image acquisition unit 11 acquires an image including the eye E. The image acquisition unit 11 is capable of acquiring an examination image, a preoperative image, and an intraoperative image. The examination image is an image including the eye E picked up by an examination apparatus (not shown) before starting surgery. The preoperative image is an image including the eye E picked up by the surgery microscope 15 when starting surgery. The intraoperative image is an image including the eye E picked up by the surgery microscope 15 during surgery.

The image acquisition unit 11 may acquire each image directly from the examination apparatus, the surgery microscope 15, or the like, and may acquire each image via a network or each image stored in storage. The image acquisition unit 11 supplies the acquired image to the magnification acquisition unit 13 and the image generation unit 14.

Figure 4:
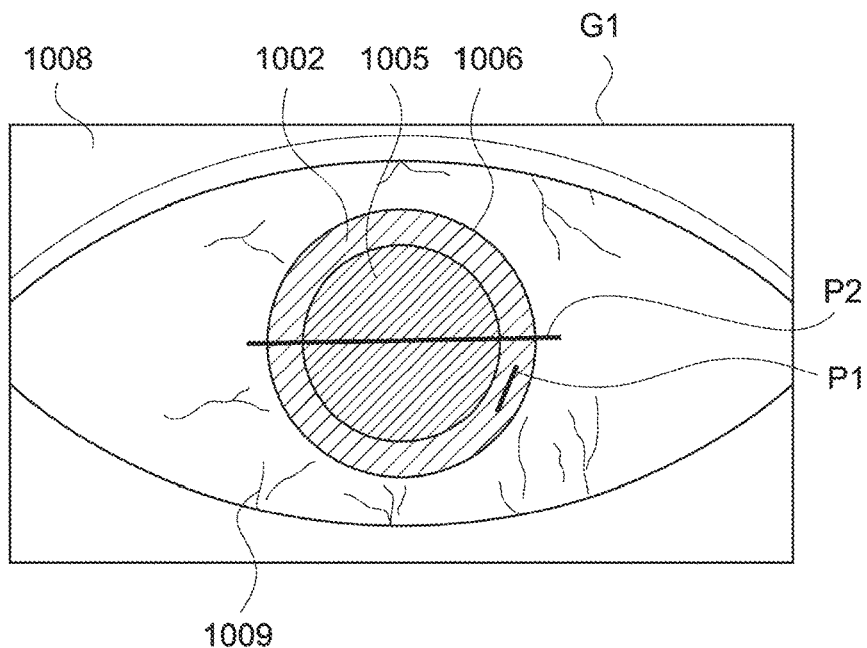
FIG. 4 An example of an examination image and preoperative planning acquired by the surgery microscope system.

The input acceptance unit 12 accepts a user input. The input acceptance unit 12 is capable of accepting specification of preoperative planning in the examination image. FIG. 4 is a schematic diagram showing an example of an examination image G1 and preoperative planning specified in the examination image G1. Note that FIG. 4 includes the pupil 1005, the iris 1002, an eye lid 1008, and a blood vessel 1009.

As shown in the figure, the preoperative planning includes an insertion position P1 of a surgical tool, an orientation P2 of an intraocular lens, and the like. A user is capable of considering the insertion position P1 of a surgical tool and the orientation P2 of an intraocular lens while referring to the examination image G1 and specifying them as preoperative planning on the examination image G1, before starting surgery. The input acceptance unit 12 accepts an input of the preoperative planning, and supplies the preoperative planning to the image generation unit 14.

The magnification acquisition unit 13 acquires the magnification between the examination image, the preoperative image, and the intraoperative image. The acquisition of the magnification will be described later. The magnification acquisition unit 13 supplies the acquired magnification to the image generation unit 14.

The image generation unit 14 generates a navigation image by using the magnification supplied from the magnification acquisition unit 13. When surgery is started and a preoperative image is picked up, the image generation unit 14 performs alignment (registration) between the examination image and the preoperative image. For this alignment, an image matching method such as SIFT (Scale-Invariant Feature Transform) is used. The image generation unit 14 is capable of using the above-mentioned magnification for alignment, and details thereof will be described later.

Figure 5:
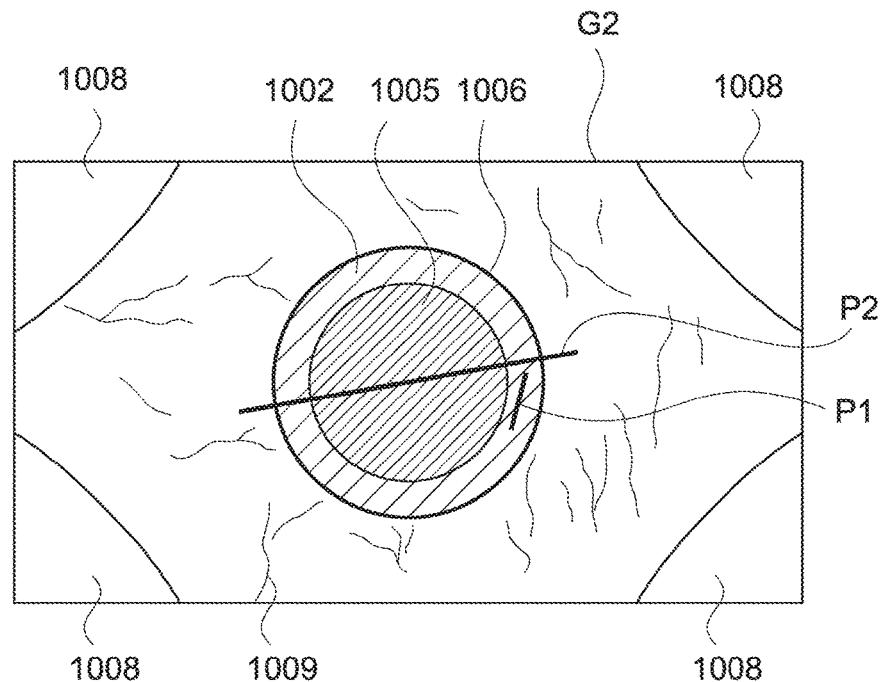
FIG. 5 An example of a navigation image output by the surgery microscope system.

The image generation unit 14 determines the arrangement in the preoperative image of preoperative planning specified on the examination image on the basis of the result of registration, superimposes the preoperative planning on the preoperative image as navigation information, and generates a navigation image. FIG. 5 is an example of the navigation image, and the insertion position P1 of a surgical tool and the orientation P2 of an intraocular lens as the navigation information are superimposed on a preoperative image G2. Note that FIG. 5 includes the pupil 1005, the iris 1002, the eye lid 1008 opened by an eyelid speculum, and the blood vessel 1009. The image generation unit 14 causes a display (not shown) to display the generated navigation image.

When surgery proceeds and an intraoperative image is picked up, the image generation unit 14 performs alignment (tracking) between the preoperative image G2 and the intraoperative image. Also for this alignment, an image matching method such as SIFT is used. The image generation unit 14 is capable of using the above-mentioned magnification for alignment, and details thereof will be described later.

The image generation unit 14 determines the arrangement in the intraoperative image of preoperative planning in the preoperative image on the basis of the result of tracking, superimposes the preoperative planning on the intraoperative image as navigation information, and generates a navigation image (see FIG. 5). The image generation unit 14 causes a display to display the navigation image to update the navigation image.

After that, the image generation unit 14 continuously acquires intraoperative images whose imaging time differs (consecutive frames or frames of arbitrary intervals), performs tracking between the intraoperative images, superimposes the preoperative planning on the intraoperative image as navigation information, and generates a navigation image.

As described above, the image generation unit 14 compares the examination image with the preoperative image in registration, and compares the preoperative image with the intraoperative image or the intraoperative images with each other in tracking. This is because the imaging conditions such as an imaging apparatus and illumination can be different between the examination image and the preoperative image, and the position of an eye, the magnification of a microscope, and the like can be different between the preoperative image and the intraoperative image or between the intraoperative images.

Hereinafter, images to be referred to in comparison, i.e., the examination image in registration and the intraoperative image whose imaging time is past in tracking are referred to as "reference image". Further, images to be compared in comparison, i.e., the preoperative image in registration and the intraoperative image whose imaging time is the latest in tracking are referred to as "target image".

The information processing apparatus 10 has the configuration described above. Note that the above-mentioned respective images do not necessarily need to be picked up by the examination apparatus or the surgery microscope, and only have to include at least an eye to be treated. Furthermore, the above-mentioned respective images may be a still image or one frame of a moving image.

[Details of Magnification Acquisition Unit]

Figure 6:
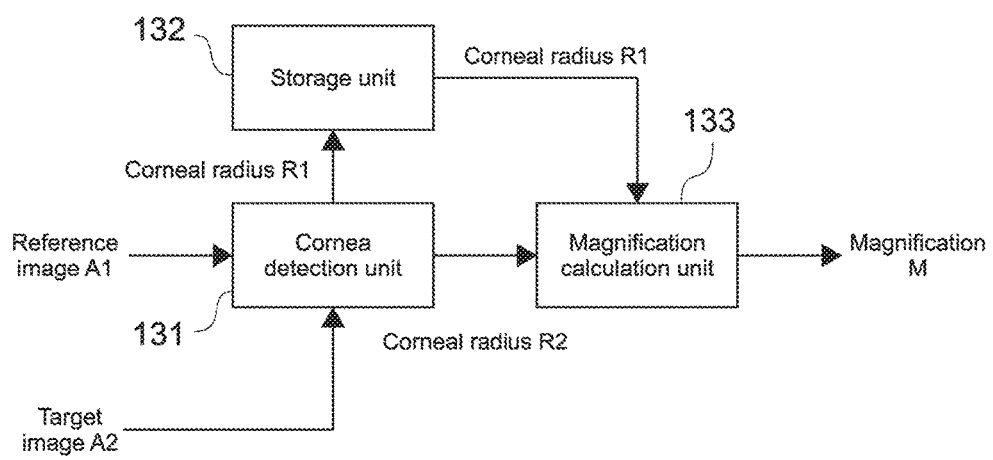
FIG. 6 A block diagram showing a configuration and operation of a magnification acquisition unit of the surgery microscope system.

As described above, the magnification acquisition unit 13 acquires the magnification of a target image with respect to a reference image. FIG. 6 is a block diagram showing a configuration and operation of the magnification acquisition unit 13. As shown in the figure, the magnification acquisition unit 13 includes a cornea detection unit 131, a storage unit 132, and a magnification calculation unit 133.

Figure 7:
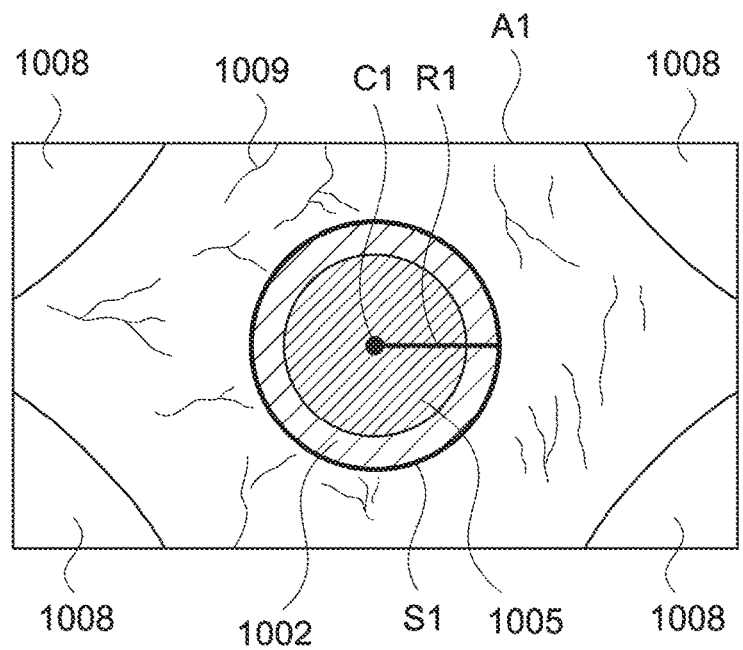
FIG. 7 A schematic diagram showing a corneal radius detected in a reference image by a cornea detection unit of the surgery microscope system.
Figure 8:
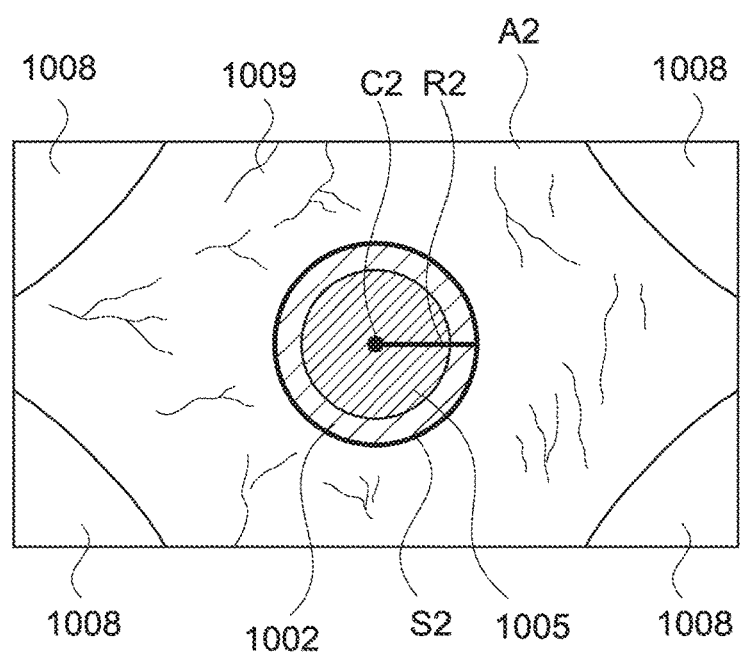
FIG. 8 A schematic diagram showing a corneal radius detected in a target image by the cornea detection unit of the surgery microscope system.

The cornea detection unit 131 detects a cornea in a reference image and a target image, and acquires a corneal center and a corneal radius. FIG. 7 is a schematic diagram showing a reference image A1, and a peripheral edge S1, a corneal center C1, and a corneal radius R1 of the cornea detected in the reference image A1. FIG. 8 is a schematic diagram showing a target image A2, and a peripheral edge S2, a corneal center C2, and a corneal radius R2 of the cornea detected in the target image A2.

The cornea detection unit 131 is capable of detecting a cornea in each image by a general image processing method such as gradient calculation, ellipse fitting, and Hough transform to acquire a corneal center and a corneal radius. The cornea detection unit 131 supplies the corneal radius R1 acquired in the reference image A1 to the storage unit 132, and the corneal radius R2 acquired in the target image A2 to the magnification calculation unit 133.

The storage unit 132 stores the corneal radius R1 supplied from the cornea detection unit 131.

The magnification calculation unit 133 acquires the corneal radius R1 from the storage unit 132 and the corneal radius R2 from the cornea detection unit 131, and calculates a magnification M by using the corneal radius R1 and the corneal radius R2. Because a corneal radius is physiologically unchanged, the change in the corneal radius in each image corresponds to the change in the magnification of the image itself. Therefore, the magnification calculation unit 133 calculates the ratio of the corneal radius R2 to the corneal radius R1, i.e., R2/R1 as the magnification M.

Figure 9:
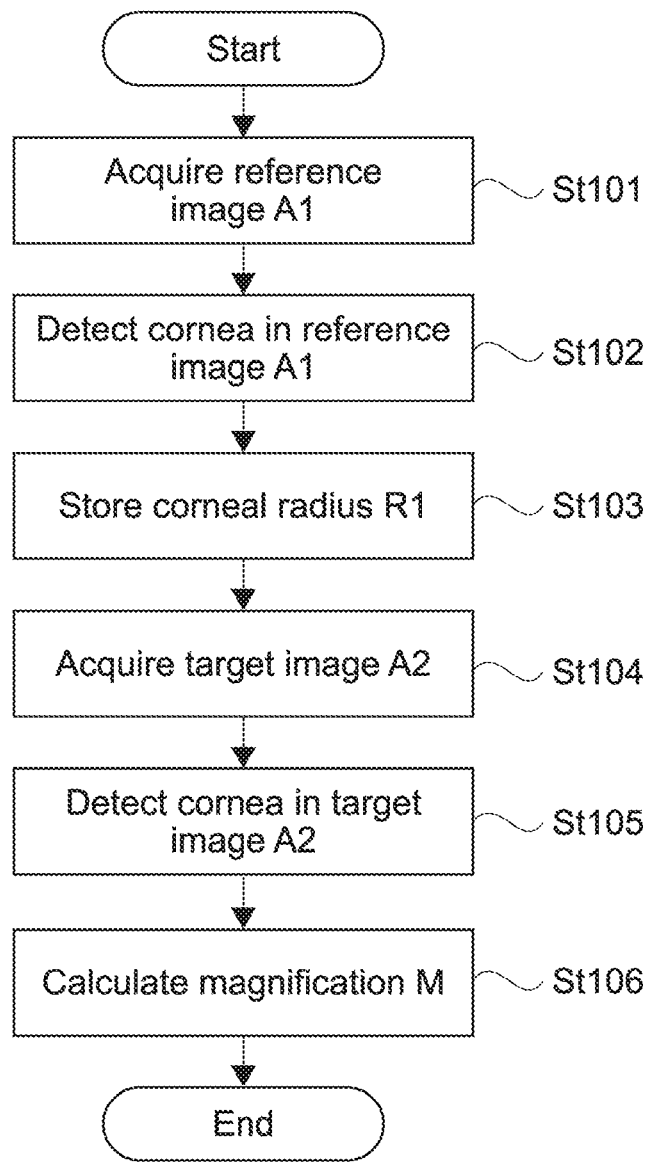
FIG. 9 A flowchart showing an operation of a magnification acquisition unit of the surgery microscope system.

FIG. 9 is a flowchart showing an operation of the magnification acquisition unit 13. As shown in the figure, the cornea detection unit 131 acquires the reference image A1 (St101), detects a cornea in the reference image A1 (St102), and stores the corneal radius R1 in the storage unit 132 (St103). Next, the cornea detection unit 131 acquires the target image A2 (St104), detects a cornea in the target image A2 (St105), and supplies it to the magnification calculation unit 133. The magnification calculation unit 123 calculates the magnification M by using the corneal radius R1 and the corneal radius R2 (St106).

The magnification acquisition unit 13 acquires the magnification M as described above, and supplies it to the image generation unit 14. Note that the cornea detection unit 131 may detect a radius of a pupil or the size of a marker made directly on an eye to be treated by a practitioner instead of a corneal radius in the reference image A1 and the target image A2. The magnification calculation unit 133 may calculate the magnification M from the ratio thereof.

The image generation unit 14 performs alignment (tracking or registration) of the reference image A1 and the target image A2 by using the magnification M as described above, and generates a navigation image. The use of the magnification M in alignment will be described in another embodiment.

[Hardware Configuration]

The functional configuration of the above-mentioned information processing apparatus 10 can be achieved by the following hardware configuration.

Figure 10:
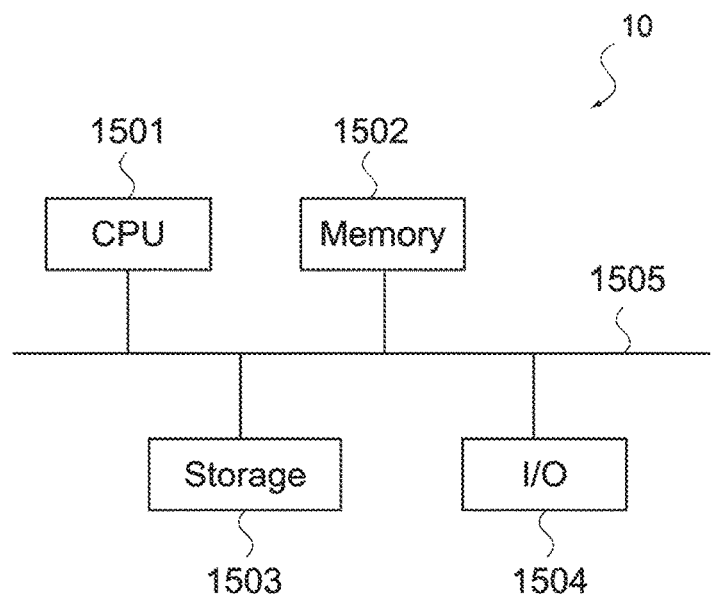
FIG. 10 A block diagram showing a hardware configuration the surgery microscope system.

FIG. 10 is a schematic diagram showing a hardware configuration of the information processing apparatus 10. As shown in the figure, the information processing apparatus 10 includes a CPU 1501, a memory 1502, a storage 1503, and an input/output unit (I/O) 1504 as a hardware configuration. These are connected to each other by a bus 1505.

The CPU (Central Processing Unit) 1501 controls another configuration in accordance with a program stored in the memory 1502, performs data processing in accordance with the program, and stores the processing result in the memory 1502. The CPU 1501 can be a microprocessor.

The memory 1502 stores a program executed by the CPU 1501 and data. The memory 1502 can be a RAM (Random Access Memory).

The storage 1503 stores a program or data. The storage 1503 can be an HDD (Hard disk drive) or an SSD (solid state drive).

The input/output unit 1504 accepts an input to the information processing apparatus 10, and supplies an output of the information processing apparatus 10 to the outside. The input/output unit 1504 includes input equipment such as a keyboard and a mouse, output equipment such as a display, and a connection interface such as a network.

The hardware configuration of the information processing apparatus 10 is not limited to those described herein as long as the functional configuration of the information processing apparatus 10 can be achieved. Further, a part or whole of the above-mentioned hardware configuration may be on a network.

Second Embodiment

A surgery microscope system according to a second embodiment of the present technology will be described.

[Configuration of Surgery Microscope System]

Figure 11:
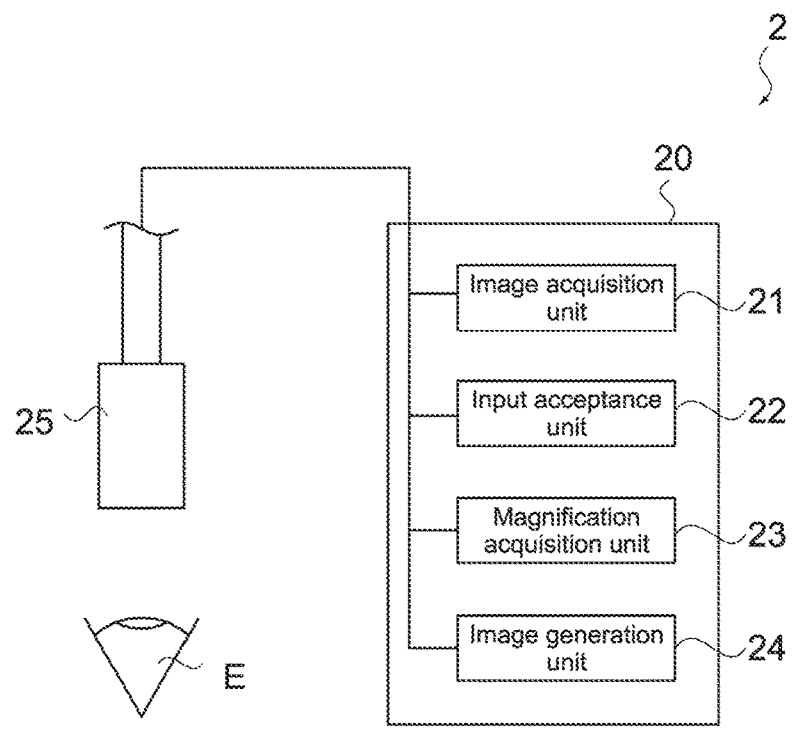
FIG. 11 A schematic diagram showing a configuration of a surgery microscope system according to a second embodiment of the present technology.

FIG. 11 is a block diagram showing a configuration of a surgery microscope system 2 according to this embodiment. As shown in the figure, the surgery microscope system 2 includes an information processing apparatus 20 and a surgery microscope 25.

The information processing apparatus 20 is an apparatus that is capable of performing information processing, such as a personal computer. The information processing apparatus 20 may be integrally formed with the surgery microscope 25, or may be an apparatus independent from the surgery microscope 25. The configuration of the information processing apparatus 20 will be described later.

As shown in FIG. 11, the surgery microscope 25 faces the eye E to be treated, and picks up a microscope magnified image of the eye E. The configuration of the surgery microscope 25 is not particularly limited as long as the surgery microscope 25 is capable of picking up an image of the eye E. The surgery microscope 25 is capable of optically or digitally changing the magnification of the image, or changing the magnification of the image also with a relative position (distance) between the surgery microscope 25 and the eye E.

[Configuration of Information Processing Apparatus]

As shown in FIG. 11, the information processing apparatus 20 includes an image acquisition unit 21, an input acceptance unit 22, a magnification acquisition unit 23, and an image generation unit 24.

The image acquisition unit 21 acquires an image including the eye E. The image acquisition unit 21 is capable of acquiring a reference image and a target image, similarly to the image acquisition unit 11 according to the first embodiment. The image acquisition unit 21 may acquire each image directly from the examination apparatus, the surgery microscope, or the like, and may acquire each image via a network or each image stored in storage. The image acquisition unit 21 supplies the acquired reference image and target image to the magnification acquisition unit 23 and the image generation unit 24.

The input acceptance unit 22 accepts an information input from a user. The input acceptance unit 22 is capable of accepting specification of preoperative planning in the examination image (see FIG. 4), similarly to the input acceptance unit 12 according to the first embodiment. The input acceptance unit 22 supplies the input preoperative planning to the image generation unit 14.

The magnification acquisition unit 23 acquires the magnification between the reference image and the target image. The acquisition of the magnification will be described later. The magnification acquisition unit 23 supplies the acquired magnification to the image generation unit 24.

The image generation unit 24 generates a navigation image including navigation information by using the magnification supplied from the magnification acquisition unit 23. The image generation unit 24 performs alignment (registration) of the examination image and the preoperative image and alignment (tracking) of the preoperative image and the intraoperative image by using an image matching method such as SIFT, similarly to the image generation unit 14 according to the first embodiment. The image generation unit 24 superimposes the navigation information (preoperative planning) on the preoperative image or the intraoperative image by using the results of alignment, and generates a navigation image (see FIG. 5). The image generation unit 24 causes a display to display the generated navigation image.

After that, the image generation unit 24 continuously acquires intraoperative images whose imaging time differs (consecutive frames or frames of arbitrary intervals), performs tracking between the intraoperative images, superimposes the preoperative planning on the intraoperative image as the navigation information, and generates a navigation image.

The information processing apparatus 20 has the configuration described above. Note that the above-mentioned respective images do not necessarily need to be picked up by the examination apparatus or the surgery microscope, and only have to include at least an eye to be treated. Furthermore, the above-mentioned respective images may be a still image or one frame of a moving image.

[Details of Magnification Acquisition Unit]

Figure 12:
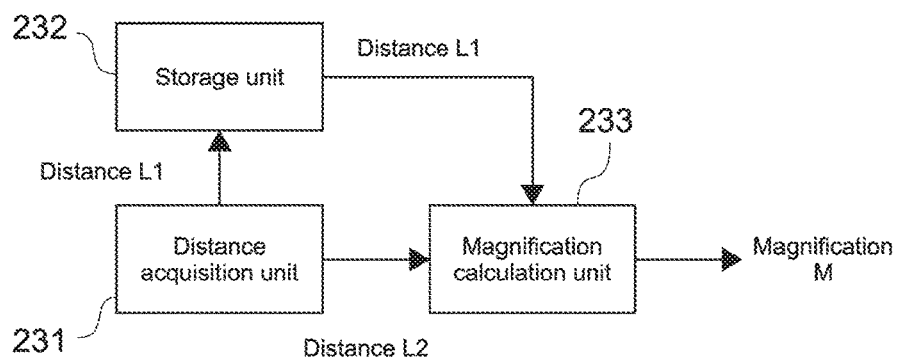
FIG. 12 A block diagram showing a configuration and operation of a magnification acquisition unit of the surgery microscope system.

As described above, the magnification acquisition unit 23 acquires the magnification of a target image with respect to a reference image. FIG. 12 is a block diagram showing a configuration and operation of the magnification acquisition unit 23. As shown in the figure, the magnification acquisition unit 23 includes a distance acquisition unit 231, a storage unit 232, and a magnification calculation unit 233.

Figure 13:
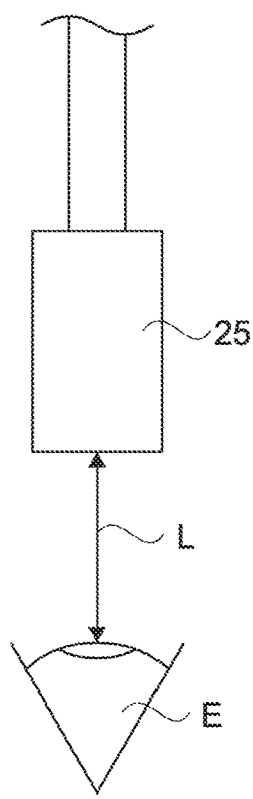
FIG. 13 A schematic diagram showing a distance between a surgery microscope and an eye to be treated acquired by the magnification acquisition unit of the surgery microscope system.

The distance acquisition unit 231 detects a distance between an imaging apparatus such as an examination apparatus and a surgery microscope and an eye to be treated. FIG. 13 is a schematic diagram showing the surgery microscope 25 and the eye E to be treated. In the figure, a distance L between the surgery microscope 25 and the eye E is shown. The distance acquisition unit 231 is capable of acquiring a three-dimensional position coordinate from an imaging apparatus, and acquiring the distance L from displacement of the three-dimensional position coordinate. Further, the distance acquisition unit 231 is also capable of acquiring the distance L on the basis of an output of a distance sensor provided to the imaging apparatus. Furthermore, in the case where the imaging apparatus includes a plurality of cameras, the distance acquisition unit 231 is also capable of acquiring the distance L from parallax information from each camera. The distance acquisition unit 231 may acquire the distance L by a method other than those described herein.

The distance acquisition unit 231 acquires at least the distance L (hereinafter, referred to as the distance L1) of the time when the reference image A1 is picked up, and the distance L (hereinafter, referred to as the distance L2) of the time when the target image A2 is picked up. The distance acquisition unit 231 supplies the distance L1 to the storage unit 342, and the distance L2 to the magnification calculation unit 233.

The storage unit 232 stores the distance L1 supplied from the distance acquisition unit 231.

The magnification calculation unit 233 acquires the distance L1 and the distance L2 from the storage unit 232 and the distance acquisition unit 231, respectively, and calculates the magnification M by using the distance L1 and the distance L2. The distance between the imaging apparatus and the eye to be treated closely relates to the magnification between images. Therefore, the magnification calculation unit 233 calculates the ratio of the distance L1 to the distance L2, i.e., L1/L2 as the magnification M.

Figure 14:
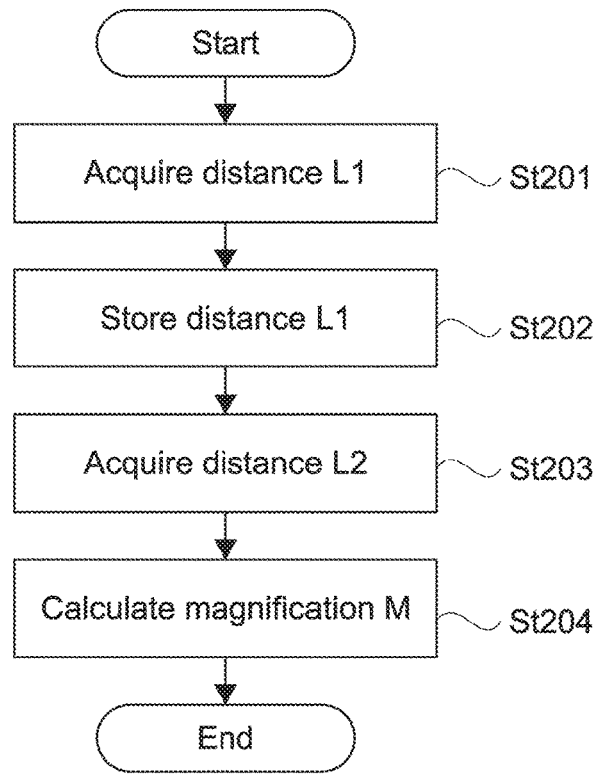
FIG. 14 A flowchart showing an operation of the magnification acquisition unit of the surgery microscope system.

FIG. 14 is a flowchart showing an operation of the magnification acquisition unit 23. As shown in the figure, the distance acquisition unit 231 acquires the distance L1 of the time when the reference image A1 is picked up (St201), and stores the distance L1 in the storage unit 232 (St202). Next, the distance acquisition unit 231 acquires the distance L2 of the time when the target image A2 is picked up (St203), and supplies it to the magnification calculation unit 233. The magnification calculation unit 233 calculates the magnification M by using the distance L1 and the distance L2 (St204).

The magnification acquisition unit 23 acquires the magnification M as described above, and supplies it to the image generation unit 24. The image generation unit 24 performs alignment (tracking or registration) of the reference image A1 and the target image A2 by using the magnification M as described above, and generates a navigation image. The use of the magnification M in alignment will be described in another embodiment.

The information processing apparatus 20 can be achieved by a hardware configuration similar to that of the information processing apparatus 10 according to the first embodiment.

Third Embodiment

A surgery microscope system according to a third embodiment of the present technology will be described.

[Configuration of Surgery Microscope System]

Figure 15:
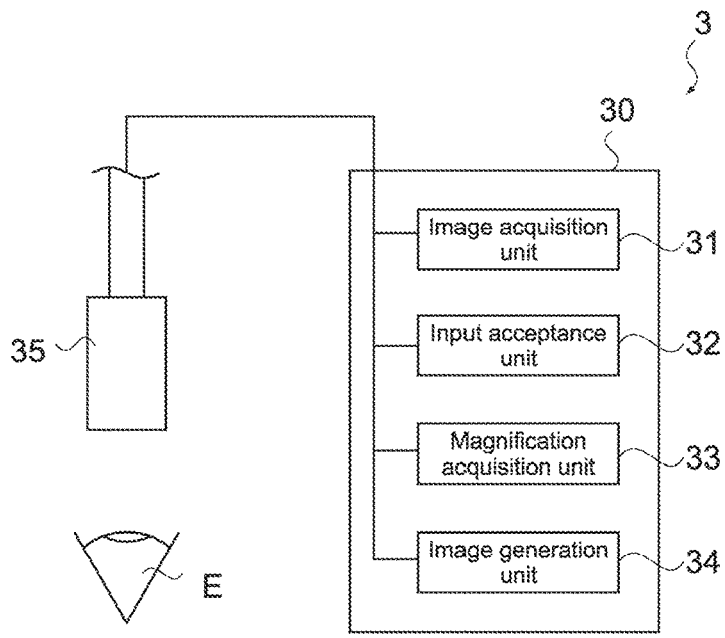
FIG. 15 A schematic diagram showing a configuration of a surgery microscope system according to a third embodiment of the present technology.

FIG. 15 is a block diagram showing a configuration of a surgery microscope system 3 according to this embodiment. As shown in the figure, the surgery microscope system 3 includes an information processing apparatus 30 and a surgery microscope 35.

The information processing apparatus 30 is an apparatus that is capable of performing information processing, such as a personal computer. The information processing apparatus 30 may be integrally formed with the surgery microscope 35, or may be an apparatus independent from the surgery microscope 35. The configuration of the information processing apparatus 30 will be described later.

As shown in FIG. 15, the surgery microscope 35 faces the eye E to be treated, and picks up a microscope magnified image of the eye E. The configuration of the surgery microscope 35 is not particularly limited as long as the surgery microscope 35 is capable of picking up an image of the eye E. The surgery microscope 35 is capable of optically or digitally changing the magnification of the image, or changing the magnification of the image also with a relative position (distance) between the surgery microscope 35 and the eye E.

[Configuration of Information Processing Apparatus]

As shown in FIG. 15, the information processing apparatus 30 includes an image acquisition unit 31, an input acceptance unit 32, a magnification acquisition unit 33, and an image generation unit 34.

The image acquisition unit 31 acquires an image including the eye E. The image acquisition unit 31 is capable of acquiring a reference image and a target image, similarly to the image acquisition unit 11 according to the first embodiment. The image acquisition unit 31 may acquire each image directly from the examination apparatus, the surgery microscope, or the like, and may acquire each image via a network or each image stored in storage. The image acquisition unit 31 supplies the acquired reference image and target image to the magnification acquisition unit 33 and the image generation unit 34.

The input acceptance unit 32 accepts an information input from a user. The input acceptance unit 32 is capable of accepting specification of preoperative planning in the examination image (see FIG. 4), similarly to the input acceptance unit 12 according to the first embodiment. The input acceptance unit 32 supplies the input preoperative planning to the image generation unit 34.

The magnification acquisition unit 33 acquires the magnification between the reference image and the target image. The acquisition of the magnification will be described later. The magnification acquisition unit 33 supplies the acquired magnification to the image generation unit 34.

The image generation unit 34 generates a navigation image including navigation information by using the magnification supplied from the magnification acquisition unit 33. The image generation unit 34 performs alignment (registration) of the examination image and the preoperative image and alignment (tracking) of the preoperative image and the intraoperative image by using an image matching method such as SIFT, similarly to the image generation unit 14 according to the first embodiment. The image generation unit 34 superimposes the navigation information (preoperative planning) on the target image by using the result of alignment, and generates a navigation image (see FIG. 5). The image generation unit 34 causes a display to display the generated navigation image.

After that, the image generation unit 34 continuously acquires intraoperative images whose imaging time differs (consecutive frames or frames of arbitrary intervals), performs tracking between the intraoperative images, superimposes the preoperative planning on the intraoperative image as the navigation information, and generates a navigation image.

The information processing apparatus 30 has the configuration described above. Note that the above-mentioned respective images do not necessarily need to be picked up by the examination apparatus or the surgery microscope, and only have to include at least an eye to be treated. Furthermore, the above-mentioned respective images may be a still image or one frame of a moving image.

[Details of Magnification Acquisition Unit]

Figure 16:
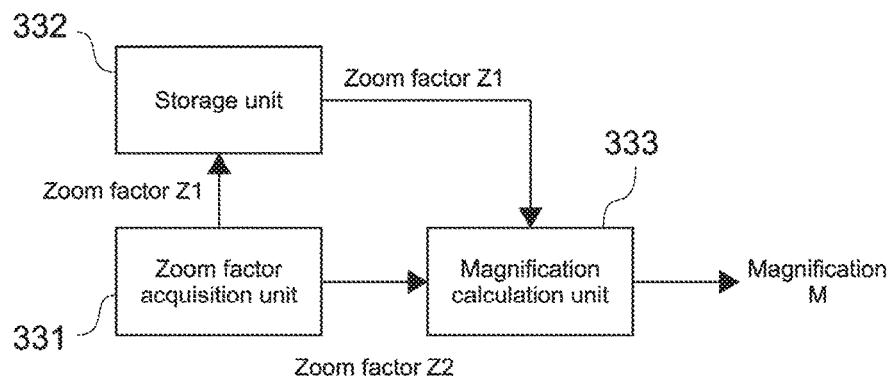
FIG. 16 A block diagram showing a configuration and operation of a magnification acquisition unit of the surgery microscope system.

As described above, the magnification acquisition unit 33 acquires the magnification of a target image with respect to a reference image. FIG. 16 is a block diagram showing a configuration and operation of the magnification acquisition unit 33. As shown in the figure, the magnification acquisition unit 33 includes a zoom factor acquisition unit 331, a storage unit 332, and a magnification calculation unit 333.

The zoom factor acquisition unit 331 acquires a zoom factor of an imaging apparatus. The zoom factor acquisition unit 331 acquires a zoom factor from an imaging apparatus such as an examination apparatus and a surgery microscope. The zoom factor is a magnification of an optical zoom and digital zoom of the imaging apparatus. The zoom factor acquisition unit 321 acquires at least a zoom factor of the time when the reference image A1 is picked up (hereinafter, referred to as the zoom factor Z1) and a zoom factor of the time when the target image A2 is picked up (hereinafter, referred to as the zoom factor Z2). The zoom factor acquisition unit 331 supplies the zoom factor Z1 to the storage unit 332, and the zoom factor Z2 to the magnification calculation unit 333.

The storage unit 332 stores the zoom factor Z1 supplied from The zoom factor acquisition unit 321.

The magnification calculation unit 333 acquires the zoom factor Z1 and the zoom factor Z2 from the storage unit 332 and the zoom factor acquisition unit 331, respectively, and calculates the magnification M by using the zoom factor Z1 and the zoom factor Z2. The zoom factor of the imaging apparatus closely relates to the magnification between images. Therefore, the magnification calculation unit 333 calculates the ratio of the zoom factor Z2 to the zoom factor Z1, i.e., Z2/Z1 as the magnification M.

Figure 17:
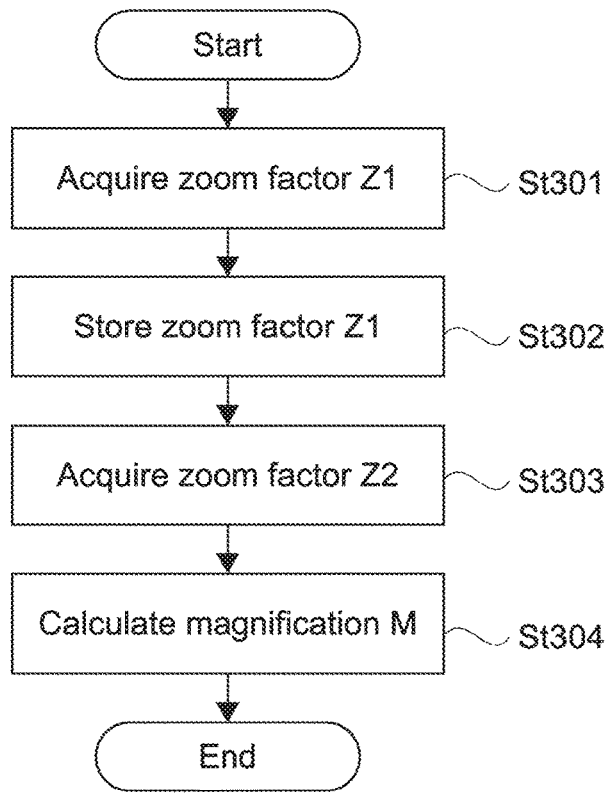
FIG. 17 A flowchart showing an operation of the magnification acquisition unit of the surgery microscope system.

FIG. 17 is a flowchart showing an operation of the magnification acquisition unit 33. As shown in the figure, the zoom factor acquisition unit 331 acquires the zoom factor Z1 of the time when the reference image A1 is picked up (St301), and stores the zoom factor Z1 in the storage unit 332 (St302). Next, the zoom factor acquisition unit 321 acquires the zoom factor Z2 of the time when the target image A2 is picked up (St303), and supplies it to the magnification calculation unit 333. The magnification calculation unit 323 calculates the magnification M by using the zoom factor Z1 and the zoom factor Z2 (St304).

The magnification acquisition unit 33 acquires the magnification M as described above, and supplies it to the image generation unit 34. The image generation unit 34 performs alignment (tracking or registration) of the reference image A1 and the target image A2 by using the magnification M as described above, and generates a navigation image. The use of the magnification M in alignment will be described in another embodiment.

The information processing apparatus 30 can be achieved by a hardware configuration similar to that of the information processing apparatus 10 according to the first embodiment.

Fourth Embodiment

A surgery microscope system according to a fourth embodiment of the present technology will be described.

[Configuration of Surgery Microscope System]

Figure 18:
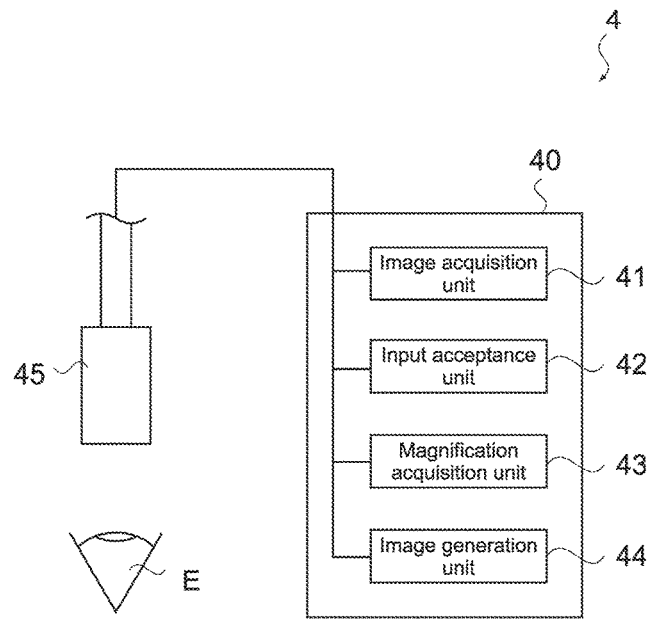
FIG. 18 A schematic diagram showing a configuration of a surgery microscope system according to a fourth embodiment of the present technology.

FIG. 18 is a block diagram showing a configuration of a surgery microscope system 4 according to this embodiment. As shown in the figure, the surgery microscope system 4 includes an information processing apparatus 40 and a surgery microscope 45.

The information processing apparatus 40 is an apparatus that is capable of performing information processing, such as a personal computer. The information processing apparatus 40 may be integrally formed with the surgery microscope 45, or may be an apparatus independent from the surgery microscope 45. The configuration of the information processing apparatus 40 will be described later.

As shown in FIG. 18, the surgery microscope 45 faces the eye E to be treated, and picks up a microscope magnified image of the eye E. The configuration of the surgery microscope 45 is not particularly limited as long as the surgery microscope 45 is capable of picking up an image of the eye E. The surgery microscope 45 is capable of optically or digitally changing the magnification of the image, or changing the magnification of the image also with a relative position (distance) between the surgery microscope 45 and the eye E.

[Configuration of Information Processing Apparatus]

As shown in FIG. 18, the information processing apparatus 40 includes an image acquisition unit 41, an input acceptance unit 42, a magnification acquisition unit 43, and an image generation unit 44.

The image acquisition unit 41 acquires an image including the eye E to be treated. The image acquisition unit 41 is capable of acquiring a reference image and a target image, similarly to the image acquisition unit 11 according to the first embodiment. The image acquisition unit 41 may acquire each image directly from the examination apparatus, the surgery microscope, or the like, and may acquire each image via a network or each image stored in storage. The image acquisition unit 41 supplies the acquired reference image and target image to the magnification acquisition unit 43 and the image generation unit 44.

The input acceptance unit 42 accepts an information input from a user. The input acceptance unit 42 is capable of accepting specification of preoperative planning in the examination image (see FIG. 4), similarly to the input acceptance unit 12 according to the first embodiment. The input acceptance unit 42 supplies the input preoperative planning to the image generation unit 44.

The magnification acquisition unit 43 acquires the magnification between the reference image and the target image. The acquisition of the magnification will be described later. The magnification acquisition unit 43 supplies the acquired magnification to the image generation unit 44.

The image generation unit 44 generates a navigation image including navigation information by using the magnification supplied from the magnification acquisition unit 43. The image generation unit 44 performs alignment (registration) of the examination image and the preoperative image and alignment (tracking) of the preoperative image and the intraoperative image by using an image matching method such as SIFT, similarly to the image generation unit 14 according to the first embodiment. The image generation unit 44 superimposes the navigation information (preoperative planning) on the preoperative image or the intraoperative image by using the result of alignment, and generates a navigation image (see FIG. 5). The image generation unit 44 causes a display to display the navigation image.

After that, the image generation unit 44 continuously acquires intraoperative images whose imaging time differs (consecutive frames or frames of arbitrary intervals), performs tracking between the intraoperative images, superimposes the preoperative planning on the intraoperative image as navigation information, and generates a navigation image.

The information processing apparatus 40 has the configuration described above. Note that the above-mentioned respective images do not necessarily need to be picked up by the examination apparatus or the surgery microscope, and only have to include at least an eye to be treated. Furthermore, the above-mentioned respective images may be a still image or one frame of a moving image.

[Details of Magnification Acquisition]

Figure 19:
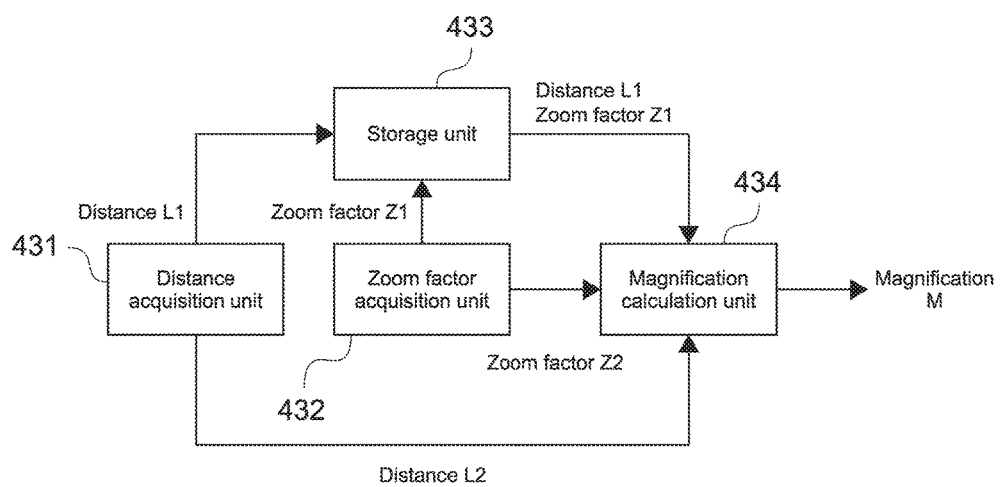
FIG. 19 A block diagram showing a configuration and operation of the magnification acquisition unit of the surgery microscope system.

As described above, the magnification acquisition unit 43 acquires the magnification of a target image with respect to a reference image. FIG. 19 is a block diagram showing a configuration and operation of the magnification acquisition unit 43. As shown in the figure, the magnification acquisition unit 43 includes a distance acquisition unit 431, a zoom factor acquisition unit 432, a storage unit 433, and a magnification calculation unit 434.

The distance acquisition unit 431 detects a distance between an imaging apparatus such as an examination apparatus and a surgery microscope and an eye to be treated. The distance acquisition unit 431 acquires, from the imaging apparatus, the distance between the imaging apparatus and the eye to be treated, similarly to the second embodiment. The distance acquisition unit 421 acquires at least the distance L1 between the imaging apparatus and the eye of the time when the reference image A1 is picked up and the distance L2 between the imaging apparatus and the eye of the time when the target image A2 is picked up. The distance acquisition unit 431 supplies the distance L1 to the storage unit 433, and the distance L2 to the magnification calculation unit 434.

The zoom factor acquisition unit 432 acquires a zoom factor of the imaging apparatus. The zoom factor acquisition unit 432 acquires the zoom factor from the imaging apparatus, similarly to the third embodiment. The zoom factor acquisition unit 432 acquires at least the zoom factor Z1 of the time when the reference image A1 is picked up and the zoom factor Z2 of the time when the target image A2 is picked up. The zoom factor acquisition unit 432 supplies the zoom factor Z1 to the storage unit 433, and the zoom factor Z2 to the magnification calculation unit 434.

The storage unit 433 stores the distance L1 supplied from the distance acquisition unit 431, and the zoom factor Z1 supplied from the zoom factor acquisition unit 432.

The magnification calculation unit 434 acquires the distance L1 and the zoom factor Z1 from the storage unit 433, the distance L2 from the distance acquisition unit 431, and the zoom factor Z2 from the zoom factor acquisition unit 432, and calculates the magnification M by using the distance L1, the distance L2, and the zoom factor Z1. The magnification calculation unit 434 calculates the product of the ratio of the distance L1 to the distance L2 and the ratio of the zoom factor Z2 to the zoom factor Z1, i.e., $(L1/L2) \times (Z2/Z1)$ as the magnification M.

Figure 20:
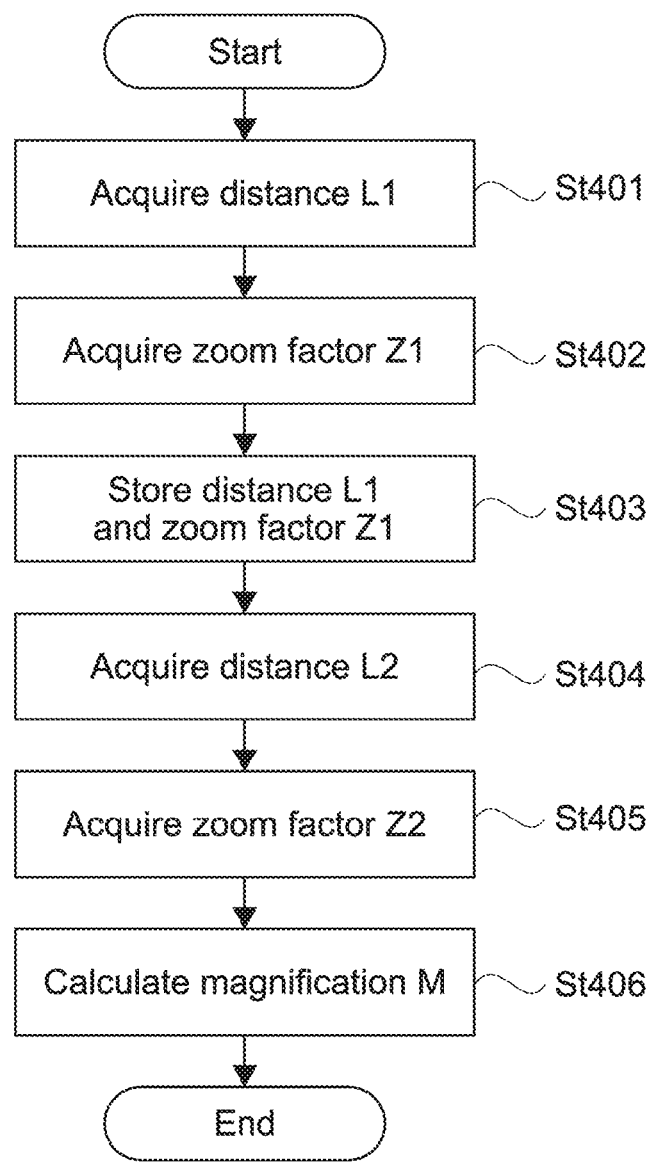
FIG. 20 A flowchart showing an operation of the magnification acquisition unit of the surgery microscope system.

FIG. 20 is a flowchart showing an operation of the magnification acquisition unit 43. As shown in the figure, the distance acquisition unit 431 acquires the distance L1 of the time when the reference image A1 is picked up (St401), and the zoom factor acquisition unit 432 acquires the zoom factor Z1 of the same time (St402). The storage unit 433 stores the distance L1 and the zoom factor Z1 (St403).

Next, the distance acquisition unit 431 acquires the distance L2 of the time when the target image A2 is picked up (St404), and supplies it to the magnification calculation unit 434. The zoom factor acquisition unit 432 acquires the zoom factor Z2 of the same time (St405), and supplies it to the magnification calculation unit 434. The magnification calculation unit 434 calculates the magnification M by using the distance L1, the distance L2, the zoom factor Z1, and the zoom factor Z2 (St406).

The magnification acquisition unit 43 acquires the magnification M as described above, and supplies it to the image generation unit 44. The image generation unit 44 performs alignment (tracking or registration) of the reference image A1 and the target image A2, and generates a navigation image by using the magnification M as described above. The use of the magnification M in alignment will be described in another embodiment.

The information processing apparatus 40 can be achieved by a hardware configuration similar to that of the information processing apparatus 10 according to the first embodiment.

Fifth Embodiment

A surgery microscope system according to a fifth embodiment of the present technology will be described.

[Configuration of Surgery Microscope System]

Figure 21:
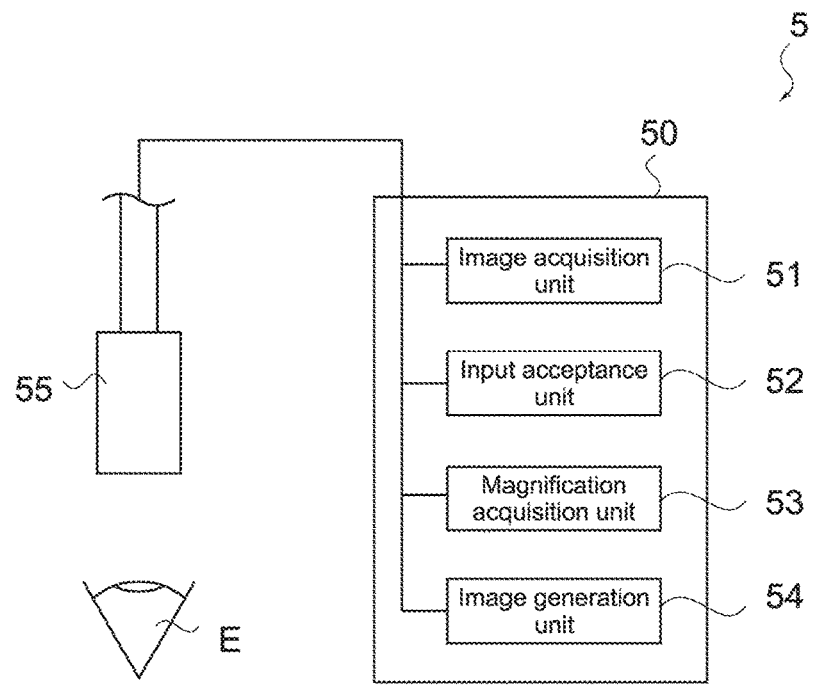
FIG. 21 A schematic diagram showing a configuration of a surgery microscope system according to a fifth embodiment of the present technology.

FIG. 21 is a block diagram showing a configuration of a surgery microscope system 5 according to this embodiment. As shown in the figure, the surgery microscope system 5 includes an information processing apparatus 50 and a surgery microscope 55.

The information processing apparatus 50 is an apparatus that is capable of performing information processing, such as a personal computer. The information processing apparatus 50 may be integrally formed with the surgery microscope 55, and may be an apparatus independent from the surgery microscope 55. The configuration of the information processing apparatus 50 will be described later.

As shown in FIG. 21, the surgery microscope 55 faces the eye E to be treated, and picks up a microscope magnified image of the eye E. The configuration of the surgery microscope 55 is not particularly limited as long as the surgery microscope 55 is capable of picking up an image of the eye E. The surgery microscope 55 is capable of optically or digitally changing the magnification of the image, or changing the magnification of the image also with a relative position (distance) between the surgery microscope 55 and the eye E.

[Configuration of Information Processing Apparatus]

As shown in FIG. 21, the information processing apparatus 50 includes an image acquisition unit 51, an input acceptance unit 52, a magnification acquisition unit 53, and an image generation unit 54.

The image acquisition unit 51 acquires an image including the eye E. The image acquisition unit 51 is capable of acquiring a reference image and a target image, similarly to the image acquisition unit 11 according to the first embodiment. The image acquisition unit 51 may acquire each image directly from the examination apparatus, the surgery microscope, or the like, and may acquire each image via a network or each image stored in storage. The image acquisition unit 41 supplies the acquired reference image and target image to the magnification acquisition unit 53 and the image generation unit 54.

The input acceptance unit 52 accepts an information input from a user. The input acceptance unit 52 is capable of accepting specification of preoperative planning in the examination image (see FIG. 4), similarly to the input acceptance unit 12 according to the first embodiment. The input acceptance unit 52 supplies the input preoperative planning to the image generation unit 34.

The magnification acquisition unit 53 acquires the magnification between the reference image and the target image. The magnification acquisition unit 53 is capable of acquiring the magnification by using any one the methods described in the embodiments 1 to 4, i.e., at least one of object recognition processing on each image, the distance between the imaging apparatus and the eye to be treated, and the zoom factor of the imaging apparatus. The magnification acquisition unit 53 supplies the acquired magnification to the image generation unit 54.

The image generation unit 54 generates a navigation image including navigation information by using the magnification supplied from the magnification acquisition unit 53. The image generation unit 54 performs alignment (registration) of the examination image and the preoperative image and alignment (tracking) of the preoperative image and the intraoperative image by using SIFT. Details thereof will be described later. The image generation unit 54 superimposes navigation information (preoperative planning) on the target image by using the results of alignment, and generates a navigation image (see FIG. 5). The image generation unit 44 causes a display to display the generated navigation image.

After that, the image generation unit 54 continuously acquires intraoperative images whose imaging time differs (consecutive frames or frames of arbitrary intervals), performs tracking between the intraoperative images, superimposes the preoperative planning on the intraoperative image as navigation information, and generates a navigation image.

The information processing apparatus 50 has the configuration described above. Note that the above-mentioned respective images do not necessarily need to be picked up by the examination apparatus or the surgery microscope, and only have to include at least an eye to be treated. Furthermore, the above-mentioned respective images may be a still image or one frame of a moving image.

[Details of Image Generation Unit]

As described above, the image generation unit 54 superimposes navigation information on the target image A2 on the basis of the magnification M, and generates a navigation image. As described above, the image generation unit 54 performs alignment (tracking or registration) of the reference image A1 and the target image A2 by using the magnification M. The image generation unit 54 is capable of performing alignment by using SIFT (Scale-Invariant Feature Transform).

SIFT is characterized by scale invariance. By using scale invariance, it is possible to perform alignment between images whose scale (i.e., magnification) differs. In SIFT, in order to detect a scale invariant characteristic point, a Gaussian filter is applied to an input image and a smoothed image is generated. At this time, a standard deviation σ of the Gaussian filter is changed little by little, and many smoothed images are prepared.

Next, a difference image (DoG: Difference of Gaussian) of smoothed images in which the standard deviations σ are adjacent to each other is generated. For example, in the case where N smoothed images are prepared, N−1 DoG images are generated. Then, by using three DoG images having consecutive standard deviations σ, determination of an extreme value of a target pixel is performed. In the previous example, because the number of extreme value detection target images is N−3, the determination of an extreme value is performed N−3 times on the target pixel.

Note that in SIFT, it needs to generate many smoothed images and search for an extreme value of a DoG image to achieve the scale invariance and computational complexity is large while alignment of images whose scales differ can be performed. Between images whose scales differ two-fold, a relationship in which the standard deviation σ of a corresponding point differs two-fold is established. As the difference between scales of the images is larger, also the difference between values of the standard deviations σ is larger, it needs to search for the standard deviation σ in a broader range, and thus, the computational complexity is increased. Meanwhile, in the case where a range ($\sigma^{min}$-$\sigma^{max}$) of the standard deviation σ to be searched for is decided in advance, it may be impossible to deal with a scale change that cannot be expressed by the standard deviation σ in this range, a corresponding characteristic point between images is lost, and thus, the precision of alignment is reduced.

Therefore, in alignment of images whose scales differ, the precision of alignment is high but the necessary computational complexity is large in the case where the range ($\sigma^{min}$-$\sigma^{max}$) of the standard deviation σ is large. In contrast, the necessary computational complexity is small but the precision of alignment is low in the case where the range ($\sigma^{min}$-$\sigma^{max}$) of the standard deviation σ is small. On the other hand, the image generation unit 54 according to this embodiment is capable of achieving alignment with high precision while suppressing the necessary computational complexity.

Figure 22A:
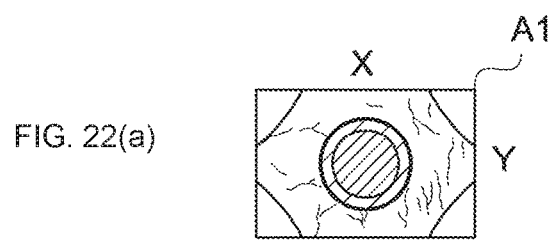
FIGS. 22(a) and 22(b) A schematic diagram showing an example of a relationship of a DoG extreme value between images whose scales differ two-fold and a method of setting a search range in SIFT.
Figure 22B:
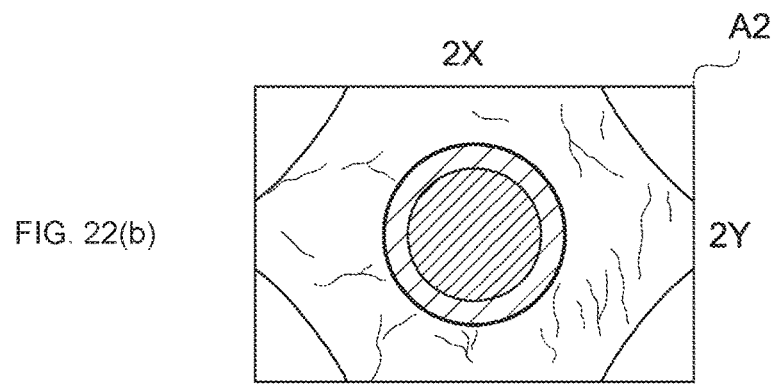

The image generation unit 54 uses the magnification M in SIFT as described above. Because the magnification M corresponds to a scale in SIFT, it is possible to increase the speed and improve the precision in SIFT by the known scale. FIGS. 22(*a*) and 22(*b*) to 24 are each a schematic diagram showing an example of a relationship of a DoG extreme value between images whose scales differ two-fold and a method of setting a search range. FIG. 22(*a*) shows the reference image A1, and FIG. 22(*b*) shows the target image A2. Note that assumption is made that the scale of the target image A2 is twice as large as (the magnification M=2) the scale of the reference image A1.

Figure 23:
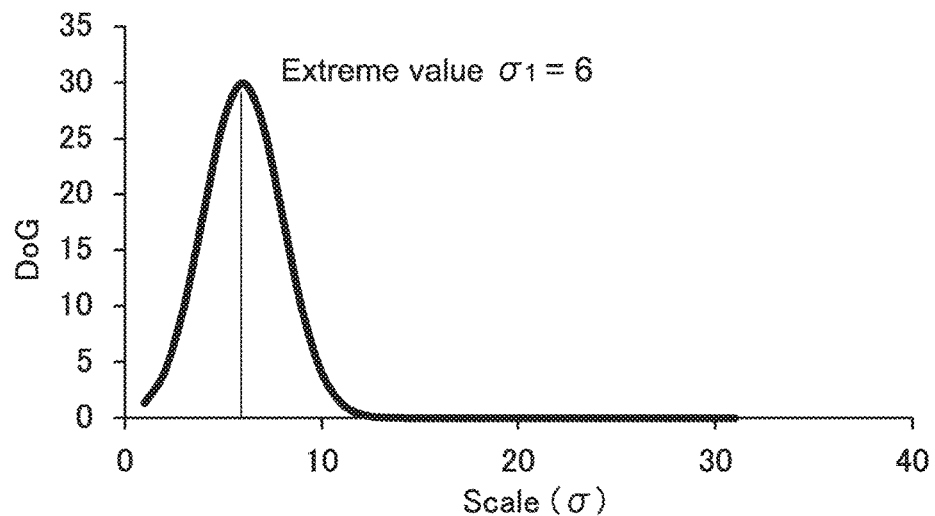
FIG. 23 A schematic diagram showing an example of a relationship of a DoG extreme value between images whose scales differ two-fold and a method of setting a search range in SIFT.
Figure 24:
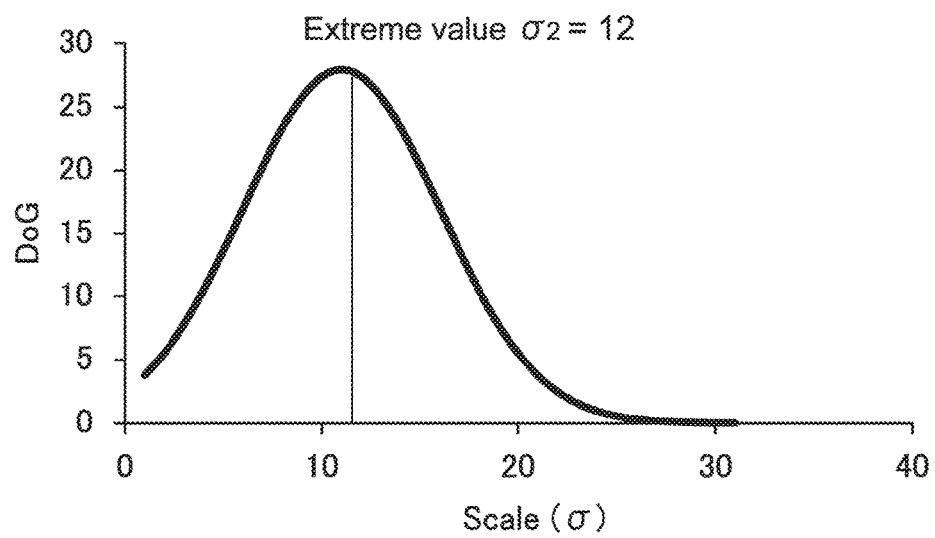
FIG. 24 A schematic diagram showing an example of a relationship of a DoG extreme value between images whose scales differ two-fold and a method of setting a search range in SIFT.

FIG. 23 is a graph showing a relationship between the standard deviation σ of the Gaussian filter and the DoG value in the target pixel of the reference image A1. As shown in the figure, a standard deviation σ1 that gives an extreme value of the DoG value is equal to 6. FIG. 24 is a graph showing a relationship between the standard deviation σ of the Gaussian filter and the DoG value in the target pixel of the target image A2. As shown in the figure, a standard deviation σ2 that gives an extreme value of the DoG value is equal to 12.

In the case where the scale between images is unknown, it needs to search for a standard deviation value ($\sigma^{min}$-$\sigma^{max}$)

in a broad range and detect an extreme value because there is no prior information related to the standard deviation σ2 that gives an extreme value of the DoG value. Meanwhile, in the case where the scale between images is known, because the standard deviation σ2 that gives an extreme value of the DoG value can be estimated, it only needs to search for only a standard deviation value in a range close thereto.

Next, the improvement of precision of alignment between images will be described. The alignment between images is performed by selecting a pair of corresponding characteristic points from a group of characteristic points detected in the images. At this time, the precision of alignment is high when many right pairs of characteristic points are selected, and the precision of alignment is low when many wrong pairs of characteristic points are selected. Examples of the processing of matching characteristic points include a method of calculating a correlation value of a characteristic amount obtained in each characteristic point and storing the characteristic point having the highest correlation value as a right pair.

However, actually, the characteristic amount is disturbed due to the influence of noise in images, or the like, and the pair having the largest correlation value is not necessarily a right pair in many cases. This causes the precision of alignment to be reduced. With respect to this problem, in the case where the scale between images is known, it is possible to increase the possibility that a right pair is selected by comparing not only the correlation values of the characteristic amount but also scale values between the characteristic points. In the examples of FIGS. 22(a) and 22(b) to 24, the pair selected as a pair having the largest correlation value of the characteristic amount can be determined to be a wrong pair when the relationship of the scale of the pair differs more than two-fold.

Figure 25:
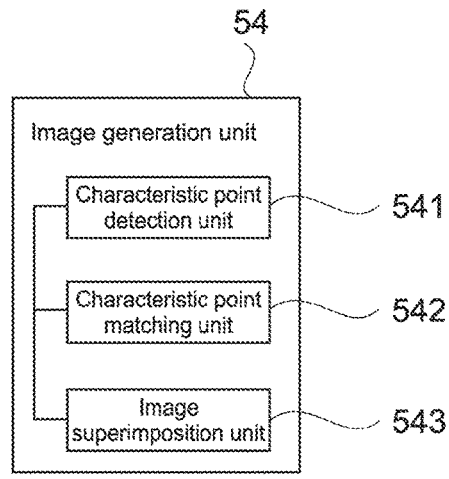
FIG. 25 A block diagram showing a configuration of an image generation unit of the surgery microscope system.

FIG. 25 is a block diagram showing a configuration of the image generation unit 54. As shown in the figure, the image generation unit 54 includes a characteristic point detection unit 541, a characteristic point matching unit 542, and an image superimposition unit 543.

Figure 26:
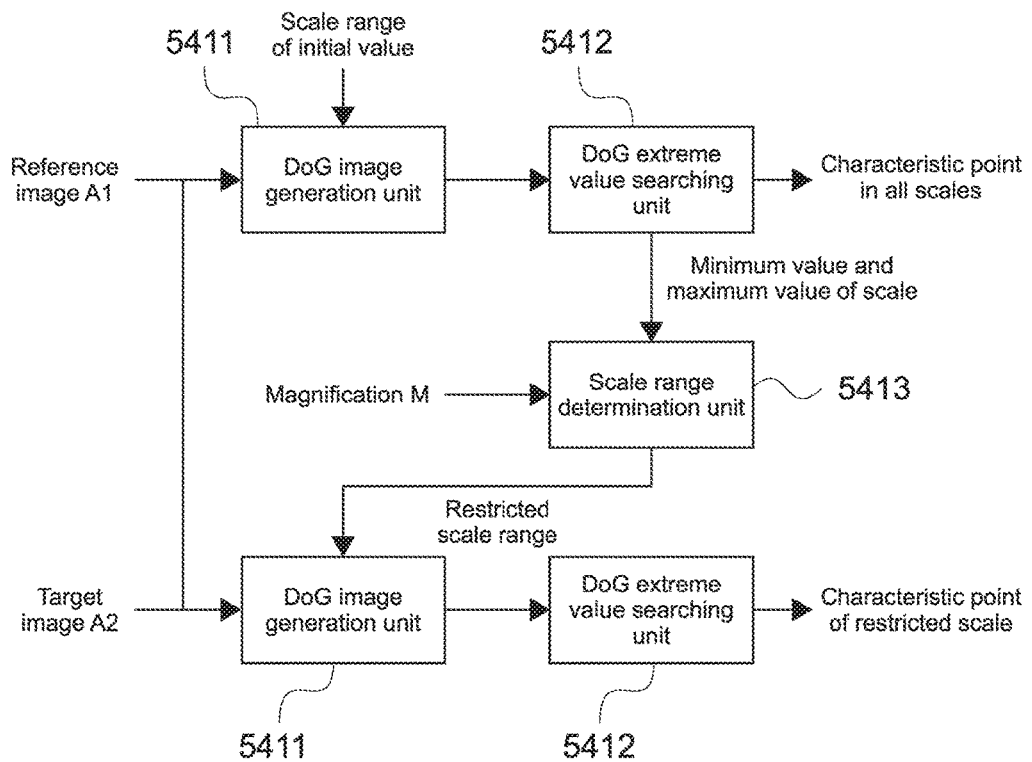
FIG. 26 A block diagram showing a configuration and operation of a characteristic point detection unit of the image generation unit of the surgery microscope system.

The characteristic point detection unit 541 detects a characteristic point in the reference image A1 and the target image A2. FIG. 26 is a block diagram showing a configuration and operation of the characteristic point detection unit 541. As shown in the figure, the characteristic point detection unit 541 includes a DoG image generation unit 5411, a DoG extreme value searching unit 5412, and a scale range determination unit 5413.

The DoG image generation unit 5411 generates a smoothed image with a scale width changed by the scale range and step width to be given, and generates a difference image (DoG image) of adjacent smoothed images. The DoG image generation unit 5411 is common to the reference image A1 and the target image A2, but the scale range to be given differs.

The DoG image generation unit 5411 uses a scale range $[\sigma^{min}_{init}, \sigma^{max}_{init}]$ defined as an initial value for the reference image A1, and a scale range $[\sigma^{min}_{A2}, \sigma^{max}_{A2}]$ defined by the scale range determination unit 5413 for the target image A2. This scale range is narrower than the scale range of the initial value, $\sigma^{min}_{A2}$ is larger than $\sigma^{min}_{init}$, and $\sigma^{max}_{A2}$ is lower than $\sigma^{max}_{init}$. Because the search range is set to be narrow for the target image A2, it is possible to achieve the increase in searching speed.

The DoG extreme value searching unit 5412 performs determination of an extreme value for each target pixel by using three consecutive DoG images, obtains a scale that gives an extreme value of the DoG value, and outputs it. The DoG extreme value searching unit 5412 is common to the reference image A1 and the target image A2, but supplies a minimum value $\sigma^{min}_{A1}$ of the scale and a maximum value $\sigma^{max}_{A1}$ of the scale in the entire image for the reference image A1 to the scale range determination unit 5413.

The scale range determination unit 5413 determines a minimum value $\sigma^{min}_{A2}$ and a maximum value $\sigma^{max}_{A2}$ of the scale for the target image A2 by the following (formula 1) and (formula 2) by using the magnification M supplied from the magnification acquisition unit 53 and the minimum value $\sigma^{min}_{A1}$ of the scale and the maximum value $\sigma^{max}_{A1}$ of the scale for the reference image A1.

$$\sigma^{min}_{A2} = M \times \sigma^{min}_{A1} \quad \text{(formula 1)}$$

$$\sigma^{max}_{A2} = M \times \sigma^{max}_{A1} \quad \text{(formula 2)}$$

The scale range determination unit 5413 supplies the scale set in the range including $[\sigma^{min}_{A2}, \sigma^{max}_{A2}]$ to the DoG image generation unit 5411.

Figure 27:
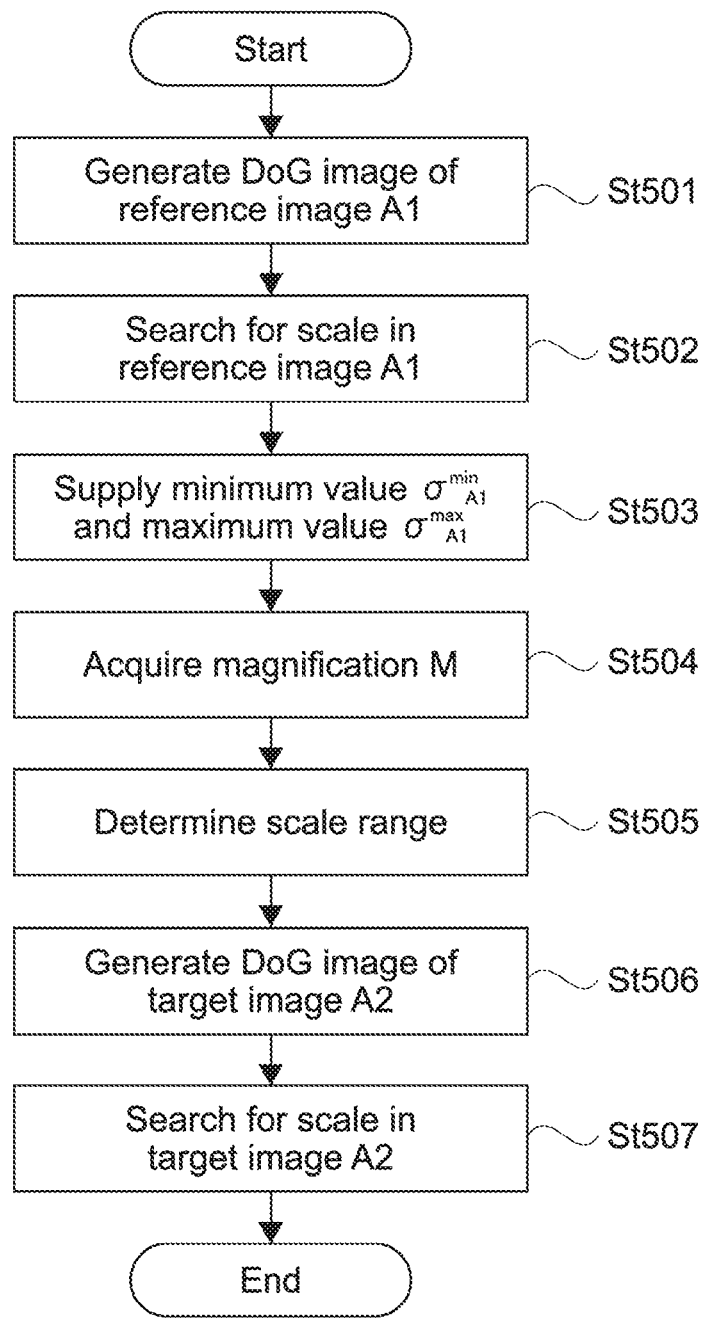
FIG. 27 A flowchart showing an operation of the characteristic point detection unit of the image generation unit of the surgery microscope system.

FIG. 27 is a flowchart of detection of a characteristic point by the characteristic point detection unit 541. As shown in the figure, the DoG image generation unit 5411 generates a DoG image of the reference image A1 (St501). Next, the DoG extreme value searching unit 5412 searches for a scale that gives an extreme value of the DoG value for each target pixel in the reference image A1 (St502). The DoG extreme value searching unit 5412 supplies the minimum value $\sigma^{min}_{A1}$ and the maximum value $\sigma^{max}_{A1}$ to the scale range determination unit 5413 (St503).

Next, the scale range determination unit 5413 acquires the magnification M from the magnification acquisition unit 53 (St504), and determines the minimum value $\sigma^{min}_{A2}$ ($=M \times \sigma^{min}_{A1}$) and the maximum value $\sigma^{max}_{A2}$ ($=M \times \sigma^{max}_{A1}$) as the scale range of the target image A2 (St505). Next, the DoG image generation unit 5411 generates a DoG image of the target image A2 (St506), and the DoG extreme value searching unit 5412 searches for a scale that gives an extreme value of the DoG value for each target pixel in the target image A2 (St507).

The characteristic point detection unit 541 detects a characteristic point in the reference image A1 and the target image A2 in this way, and supplies it to the characteristic point matching unit 542.

Figure 28:
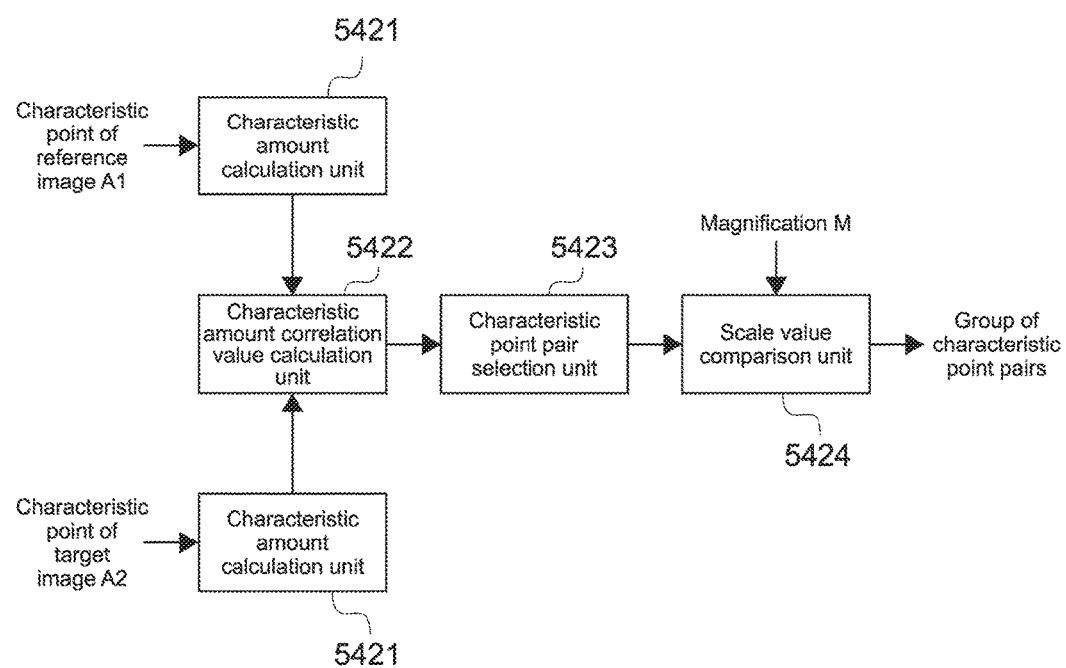
FIG. 28 A block diagram showing a configuration and operation of a characteristic point matching unit of the image generation unit of the surgery microscope system.

The characteristic point matching unit 542 performs matching of the characteristic point detected in the reference image A1 and the target image A2. FIG. 28 is a block diagram showing a configuration and operation of the characteristic point matching unit 542. As shown in the figure, the characteristic point matching unit 542 includes a characteristic amount calculation unit 5421, a characteristic amount correlation value calculation unit 5422, a characteristic point pair selection unit 5423, and a scale value comparison unit 5424.

The characteristic amount calculation unit 5421 is common to the reference image A1 and the target image A2, calculates the characteristic amount for each characteristic point in both images, and supplies it to the characteristic amount correlation value calculation unit 5422.

The characteristic amount correlation value calculation unit 5422 calculates the correlation value of the characteristic amounts between the target characteristic point of the reference image A1 and each characteristic point of the target image A2, and supplies it to the characteristic point pair selection unit 5423.

The characteristic point pair selection unit 5423 calculates the characteristic point of the target image A2 having the largest correlation value with respect to each characteristic point of the reference image A1, and supplies it to the scale value comparison unit 5424 as a characteristic point pair.

The scale value comparison unit 5424 determines whether or not the characteristic pair is right by using the magnification M supplied from the magnification acquisition unit 53. The scale value comparison unit 5424 compares the scale values of each characteristic point pair by the following (formula 3).

$$S_1 \times M < \sigma_{A2}/\sigma_{A1} < S_2 \times M \qquad \text{(formula 3)}$$

$\sigma_{A1}$ is a scale of a characteristic point of the reference image A1, $\sigma_{A2}$ is a scale of a characteristic point of the target image A2, and $S_1$ and $S_2$ are each a parameter for correcting the magnification. $S_1$ is for controlling an allowable range of the lower limit of a scale ratio, and $S_2$ is for controlling an allowable range of the upper limit of a scale ratio. A characteristic point pair that satisfies the above-mentioned (formula 3) is stored as a right characteristic point pair, and a characteristic point pair that does not satisfy the above-mentioned (formula 3) is discarded as a wrong characteristic point pair.

Figure 29:
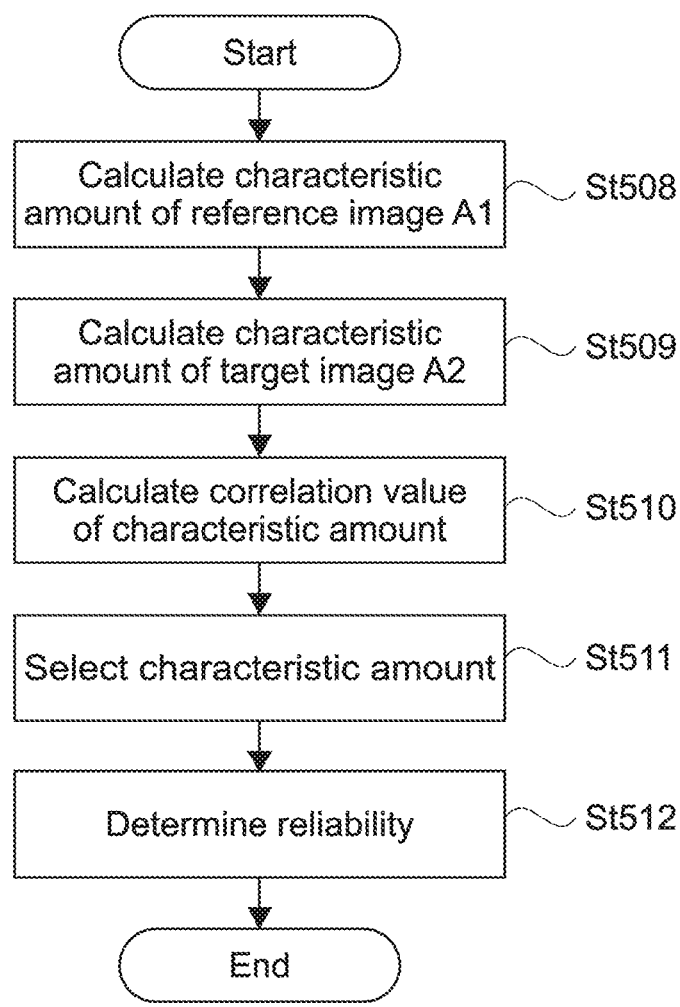
FIG. 29 A flowchart showing an operation of the characteristic point matching unit of the image generation unit of the surgery microscope system.

FIG. 29 is a flowchart of matching of a characteristic point by the characteristic point matching unit 542. The characteristic amount calculation unit 5421 calculates the characteristic amount for each characteristic point in the reference image A1 (St508). Next, the characteristic amount calculation unit 5421 calculates the characteristic amount for each characteristic point in the target image A2 (St509). The characteristic amount correlation value calculation unit 5422 calculates a correlation value of the characteristic amount between a target characteristic point in the reference image A1 and all characteristic points of the target image A2 (St510).

Next, the characteristic point pair selection unit 5423 selects a characteristic point of the target image A2 having the largest correlation value with respect to each characteristic point of the reference image A1 (St511). The scale value comparison unit 5424 calculates a ratio of a scale value for a characteristic point pair, and determines the reliability of the characteristic point pair (St512).

The characteristic point matching unit 542 extracts a characteristic point pair having high reliability in this way, and supplies it to the image superimposition unit 533.

The image superimposition unit 543 performs alignment of the reference image A1 and the target image A2 by using the characteristic point pair supplied from the characteristic point matching unit 542, superimposes navigation information (preoperative planning) on the target image A2, and generates a navigation image.

The image generation unit 54 has the configuration described above. As described above, the characteristic point detection unit 541 is capable of achieving the increase in the searching speed by using the magnification M. Further, the characteristic point matching unit 542 is capable of improving the precision of the characteristic point pair by using the magnification M.

The information processing apparatus 50 can be achieved by a hardware configuration similar to that of the information processing apparatus 10 according to the first embodiment.

Sixth Embodiment

A surgery microscope system according to a sixth embodiment of the present technology will be described.

[Configuration of Surgery Microscope System]

Figure 30:
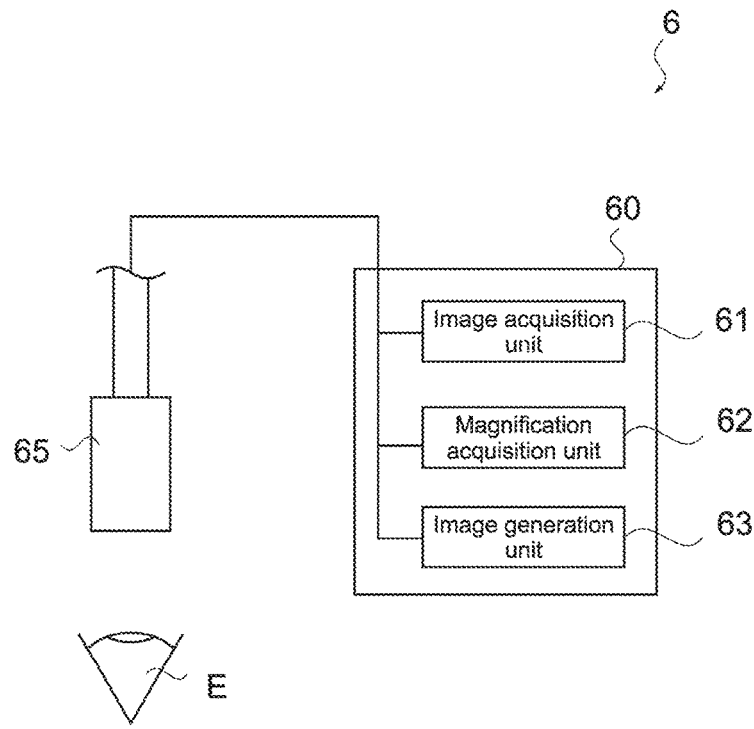
FIG. 30 A schematic diagram showing a configuration of a surgery microscope system according to a sixth embodiment of the present technology.

FIG. 30 is a block diagram showing a configuration of a surgery microscope system 6 according to this embodiment. As shown in the figure, the surgery microscope system 6 includes an information processing apparatus 60 and a surgery microscope 65.

The information processing apparatus 60 is an apparatus that is capable of performing information processing, such as a personal computer. The information processing apparatus 60 may be integrally formed with the surgery microscope 65, or may be an apparatus independent from the surgery microscope 65. The configuration of the information processing apparatus 60 will be described later.

As shown in FIG. 30, the surgery microscope 65 faces the eye E to be treated, and picks up a microscope magnified image of the eye E. The configuration of the surgery microscope 65 is not particularly limited as long as the surgery microscope 65 is capable of picking up an image of the eye E. The surgery microscope 65 is capable of optically or digitally changing the magnification of the image, or changing the magnification of the image also with a relative position (distance) between the surgery microscope 65 and the eye E.

[Configuration of Information Processing Apparatus]

As shown in FIG. 30, the information processing apparatus 60 includes an image acquisition unit 61, a magnification acquisition unit 62, and an image generation unit 63.

The image acquisition unit 61 acquires an image including the eye E. The image acquisition unit 61 is capable of acquiring a reference image and a target image, similarly to the image acquisition unit 11 according to the first embodiment. The image acquisition unit 61 may acquire each image directly from the examination apparatus, the surgery microscope, or the like, and may acquire each image via a network or each image stored in storage. The image acquisition unit 61 supplies the acquired image to the magnification acquisition unit 62 and the image generation unit 63.

The magnification acquisition unit 62 acquires the magnification between the reference image and the target image. The magnification acquisition unit 62 is capable of acquiring the magnification by using any one the methods described in the embodiments 1 to 4, i.e., at least one of object recognition processing on each image, the distance between the imaging apparatus and the eye to be treated, and the zoom factor of the imaging apparatus. The magnification acquisition unit 62 supplies the acquired magnification to the image generation unit 63.

The image generation unit 63 generates a navigation image including navigation information by using the magnification supplied from the magnification acquisition unit 62. The image generation unit 63 selects, as navigation information, information that is different depending on the magnification, and generates a navigation image. Details thereof will be described later. The image generation unit 63 causes a display to display the navigation image.

The information processing apparatus 50 has the configuration described above. Note that the above-mentioned respective images do not necessarily need to be picked up by the examination apparatus or the surgery microscope, and only have to include at least an eye to be treated. Furthermore, the above-mentioned respective images may be a still image or one frame of a moving image.

[Details of Image Generation Unit]

As described above, the image generation unit 63 selects navigation information on the basis of the magnification M, and generates navigation information.

Figure 31:
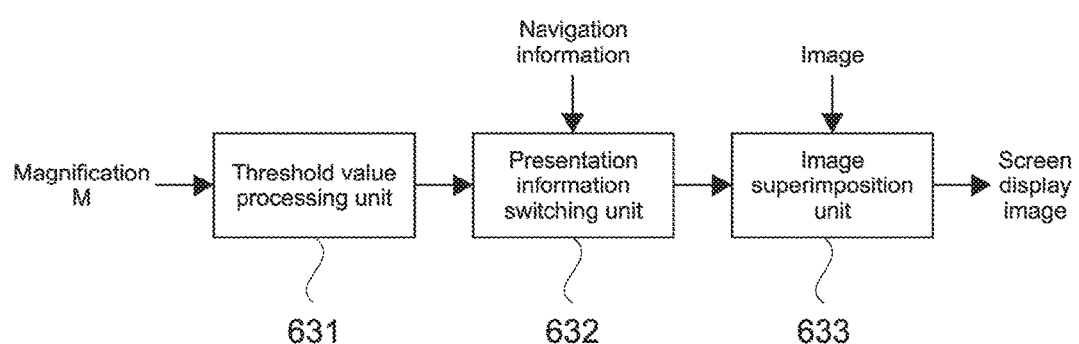
FIG. 31 A block diagram showing a configuration and operation of an image generation unit of the surgery microscope system.

FIG. 31 is a block diagram showing a configuration and operation of the image generation unit 63. As shown in the figure, the image generation unit 63 includes a threshold value processing unit 631, a presentation information switching unit 632, and an image superimposition unit 633.

When the magnification M is supplied to the threshold value processing unit 631, the threshold value processing unit 631 performs threshold value processing on the magnification M, and selects an identifier of navigation information to be presented. The number of threshold values may be one or more. The threshold value processing unit 631 supplies the selected identifier to the presentation information switching unit 632.

The presentation information switching unit 632 selects navigation information identified by the identifier supplied from the threshold value processing unit 631 out of navigation information stored in the storage unit, and supplies it to the image superimposition unit 633.

The image superimposition unit 633 superimposes the navigation information supplied from the presentation information switching unit 632 on a target image, and generates a navigation image. The image superimposition unit 633 is capable of detecting a tissue (cornea or the like) of the eye by image processing on the target image, and superimposing the navigation information on the target image depending on the position thereof.

Figure 32:
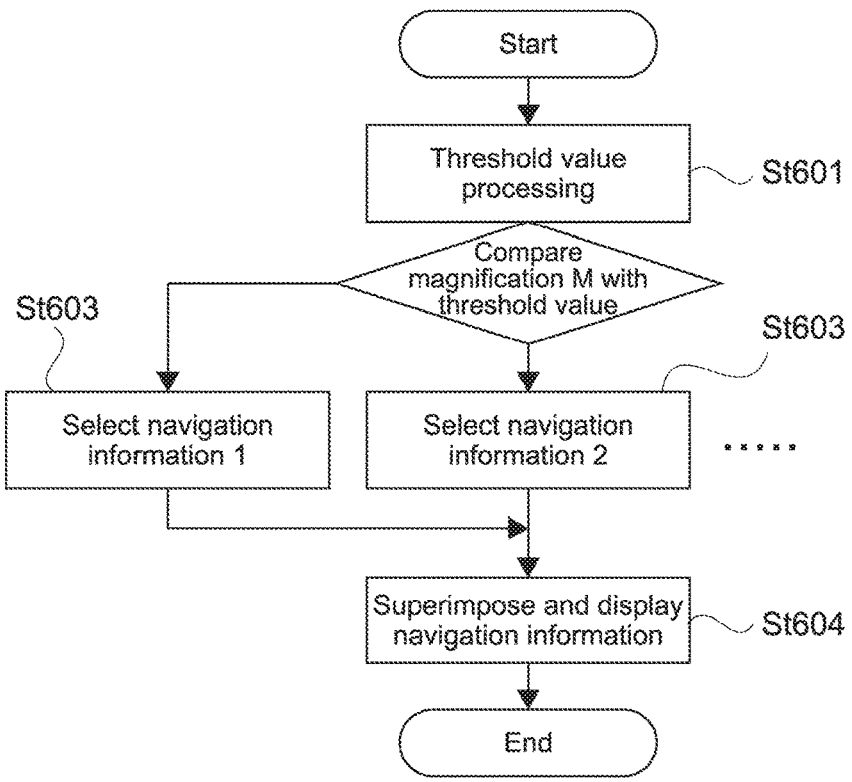
FIG. 32 A flowchart showing an operation of the image generation unit of the surgery microscope system.

FIG. 32 is a flowchart showing an operation of the image generation unit 63. As shown in the figure, when the magnification M is supplied to the threshold value processing unit 631, the threshold value processing unit 631 performs threshold value processing on the magnification M (St601). Specifically, the threshold value processing unit 631 selects an identifier of navigation information to be presented depending on the magnitude relationship between the magnification M and the threshold value (St601), and supplies the selected identifier to the presentation information switching unit 632. The presentation information switching unit 632 selects the navigation information identified by identifier supplied from the threshold value processing unit 631 (St603), and supplies it to the image superimposition unit 633. The image superimposition unit 633 superimposes the supplied navigation information on the target image, generates a navigation image, and causes a display to display the navigation image (St604).

Figure 33:
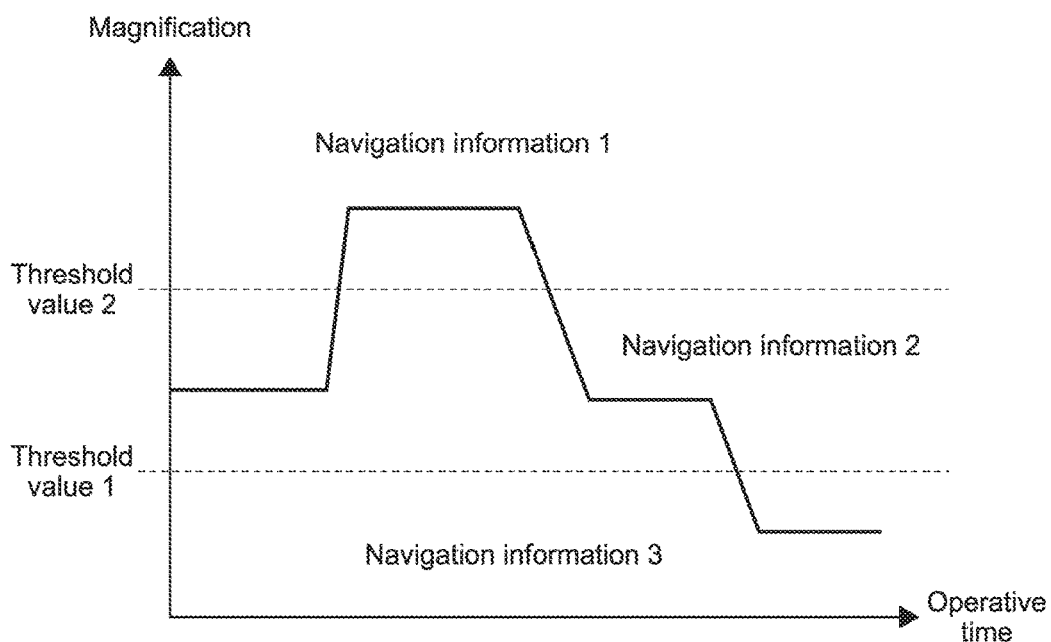
FIG. 33 A graph showing navigation information selected by an image generation unit of the surgery microscope system.

FIG. 33 is an example of a switching operation of navigation information by the image generation unit 63. The threshold value processing unit 631 selects a different identifier depending on the change in the magnification M with elapse of operative time, and the presentation information switching unit 632 selects navigation to be presented depending on the identifier. For example, as shown in FIG. 33, navigation information 1 is selected in the case where the magnification M is not less than a threshold value 2, and navigation information 2 is selected in the case where the magnification M is not less than a threshold value 1 and less than the threshold value 2. Further, navigation information 3 is selected in the case where the magnification M is less than the threshold value 1.

Figure 34A:
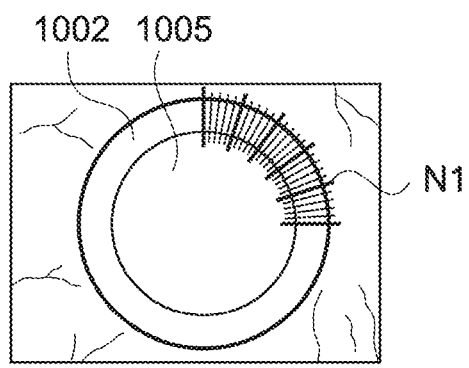
FIGS. 34(a), 34(b) and 34(c) An example of a navigation image generated by the image generation unit of the surgery microscope system.
Figure 34B:
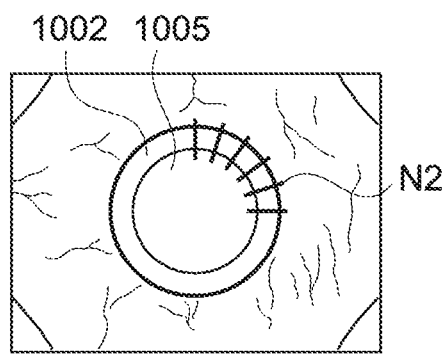
Figure 34C:
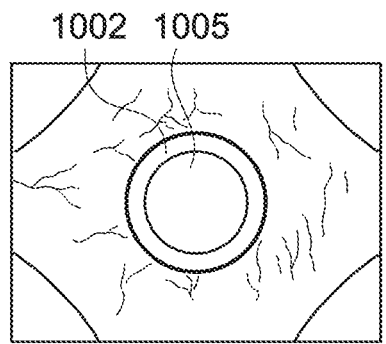

FIGS. 34(*a*), 34(*b*) and 34(*c*) are example of a navigation image generated by the image generation unit 63. In the figure, navigation information is an angle scale arranged on the periphery of a cornea. FIG. 34(*a*) shows the case where the magnification M is not less than the threshold value 2, and the navigation information 1 (N1) is included. This navigation information 1 includes a scale arranged at predetermined intervals. FIG. 34(*b*) shows the case where the magnification M is not less than the threshold value 1 and less than the threshold value 2, and the navigation information 2 (N2) is included. The scale interval of the navigation information 2 is larger than that of the navigation information 1. FIG. 34(*c*) shows the case where the magnification M is less than the threshold value 1, and the navigation information 3 (not displayed) is included.

As described above, the image generation unit 63 switches navigation information to be displayed depending on the magnitude of the magnification M. It is considered that when a user performs a zoom-in operation in which the magnification M is increased, the user intends to check the insertion angle of an intraocular lens in more detail. In order to support this, navigation information including a finer angle scale is displayed. Further, it is considered that when a user performs a zoom-out operation in which the magnification M is decreased, the user intends to check presence or absence of bleeding or the entire eye in the overhead view. In this case, navigation information is not displayed because it is unnecessary to display an angle scale.

Note that the navigation information is not limited to an angle scale, and only needs to be switched depending on the change in the magnification M. Further, the image superimposition unit 633 does not necessarily need to superimpose navigation information on an image depending on the position of a tissue of an eye, and may superimpose navigation information on an image regardless of the position of a tissue of an eye.

The image generation unit 63 has the configuration described above. As described above, the image generation unit 63 generates a navigation image including navigation information that is different depending on the magnification M. Because the navigation information is automatically selected depending on the magnification M, the user does not need to manually select it, and it is possible to provide high convenience.

Seventh Embodiment

A surgery microscope system according to a seventh embodiment of the present technology will be described.

[Configuration of Surgery Microscope System]

Figure 35:
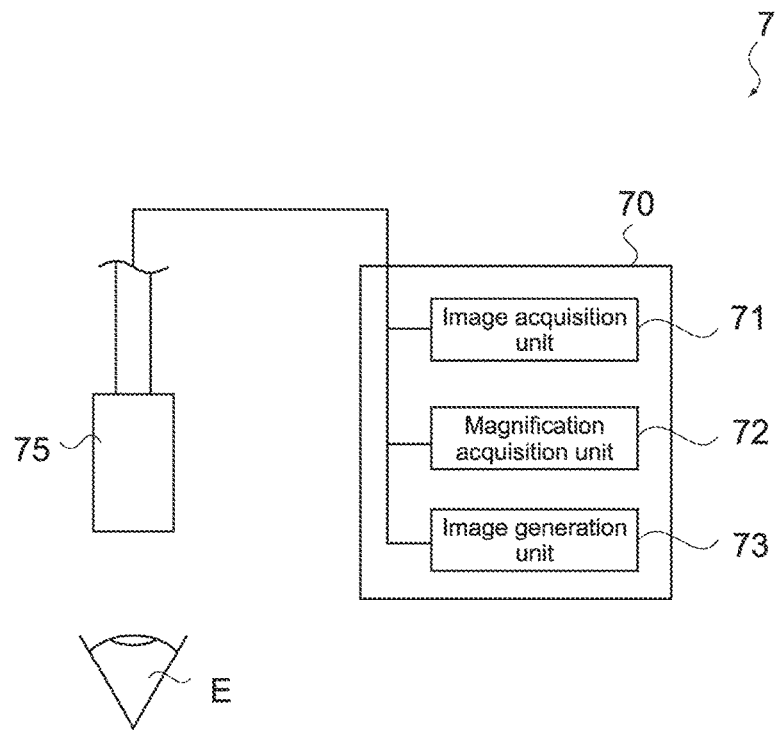
FIG. 35 A schematic diagram showing a configuration of a surgery microscope system according to a seventh embodiment of the present technology.

FIG. 35 is a block diagram showing a configuration of a surgery microscope system 7 according to this embodiment. As shown in the figure, the surgery microscope system 7 includes an information processing apparatus 70 and a surgery microscope 75.

The information processing apparatus 70 is an apparatus that is capable of performing information processing, such as a personal computer. The information processing apparatus 70 may be integrally formed with the surgery microscope 75, and may be an apparatus independent from the surgery microscope 75. The configuration of the information processing apparatus 70 will be described later.

As shown in FIG. 35, the surgery microscope 75 faces the eye E to be treated, and picks up a microscope magnified image of the eye E. The configuration of the surgery microscope 75 is not particularly limited as long as the surgery microscope 75 is capable of picking up an image of the eye E. The surgery microscope 75 is capable of optically or digitally changing the magnification of the image, or changing the magnification of the image also with a relative position (distance) between the surgery microscope 75 and the eye E.

[Configuration of Information Processing Apparatus]

As shown in FIG. 35, the information processing apparatus 70 includes an image acquisition unit 71, a magnification acquisition unit 72, and an image generation unit 73.

The image acquisition unit 71 acquires an image including the eye E. The image acquisition unit 71 is capable of acquiring a reference image and a target image, similarly to the image acquisition unit 11 according to the first embodiment. The image acquisition unit 71 may acquire each image directly from the examination apparatus, the surgery microscope, or the like, and may acquire each image via a network or each image stored in storage. The image acquisition unit 71 supplies the acquired image to the magnification acquisition unit 72 and the image generation unit 73.

The magnification acquisition unit 72 acquires the magnification between the reference image and the target image. The magnification acquisition unit 72 is capable of acquiring the magnification by using any one the methods described in the embodiments 1 to 4, i.e., at least one of object recognition processing on each image, the distance between the imaging apparatus and the eye to be treated, and the zoom factor of the imaging apparatus. The magnification acquisition unit 72 supplies the acquired magnification to the image generation unit 73.

The image generation unit 73 performs image processing by using the magnification supplied from the magnification acquisition unit 72, and generates a display image. Details thereof will be described later. The image generation unit 73 causes a display to display the display image generated by the image processing.

The information processing apparatus 70 has the configuration described above. Note that the above-mentioned respective images do not necessarily need to be picked up by the examination apparatus or the surgery microscope, and only have to include at least an eye to be treated. Furthermore, the above-mentioned respective images may be a still image or one frame of a moving image.

[Details of Image Generation Unit]

As described above, the image generation unit 73 performs image processing on a target image depending on the magnification M.

Figure 36:
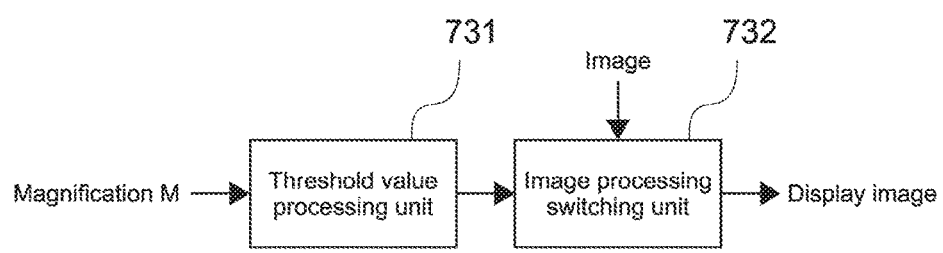
FIG. 36 A block diagram showing a configuration and operation of an image generation unit of the surgery microscope system.

FIG. 36 is a block diagram showing a configuration and operation of the image generation unit 73. As shown in the figure, the image generation unit 73 includes a threshold value processing unit 731 and an image processing switching unit 732.

When the magnification M is supplied to the threshold value processing unit 731, the threshold value processing unit 731 performs threshold value processing on the magnification M, and selects a kind of image processing. The number of threshold values may be one or more. Examples of the kind of image processing include, but not particularly limited to, shadow emphasis processing, processing for improving definition, and blood vessel emphasis processing. The threshold value processing unit 731 supplies the selected kind of image processing to the image processing switching unit 732.

The image processing switching unit 732 performs image processing whose kind is selected by the threshold value processing unit 731 on the target image.

Figure 37:
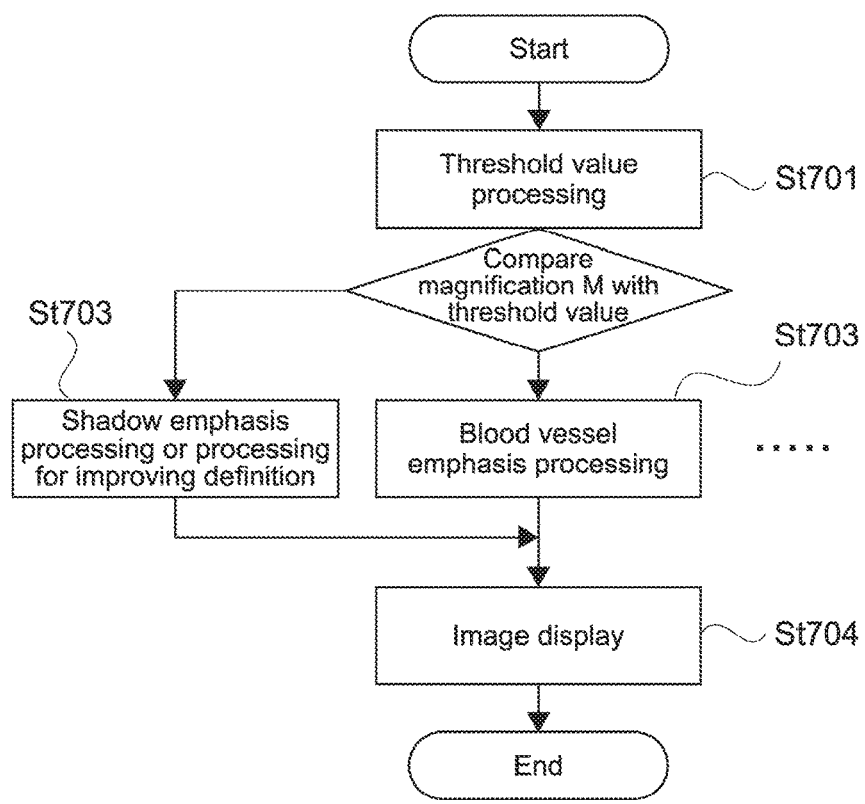
FIG. 37 A flowchart showing an operation of the image generation unit of the surgery microscope system.

FIG. 37 is a flowchart showing an operation of the image generation unit 73. As shown in the figure, when the magnification M is supplied to the threshold value processing unit 731, the threshold value processing unit 731 performs threshold value processing on the magnification M (St701). Specifically, the threshold value processing unit 631 selects a kind of image processing depending on the result of comparing the magnification M with a threshold value (St701), and supplies the selected kind of image processing to the image processing switching unit 732. The image processing switching unit 732 performs image processing whose kind is selected by the threshold value processing unit 731 on the target image (St703), and causes a display to display it (St704).

As described above, the image generation unit 73 performs, on a target image, image processing that is different depending on the magnitude of the magnification M. It is considered that when a user performs a zoom-in operation in which the magnification M is increased, the user intends to check the inside of a cornea in detail. In this regard, in order to improve the visibility inside the cornea, the image generation unit 73 applies image processing such as shadow emphasis and definition improvement. Further, it is considered that when a user performs a zoom-out operation in which the magnification M is decreased, the user intends to check presence or absence of bleeding or the entire eye in the overhead view. In this regard, the image generation unit 73 applies image processing such as blood vessel emphasis.

The image generation unit 73 has the configuration described above. As described above, the image generation unit 73 performs, on a target image, image processing that is different depending on the magnification M, and generates a navigation image. Because the kind of image processing is automatically selected depending on the magnification M, the user does not need to manually select it, and it is possible to provide high convenience.

Eighth Embodiment

A surgery microscope system according to an eighth embodiment of the present technology will be described.

[Configuration of Surgery Microscope System]

Figure 38:
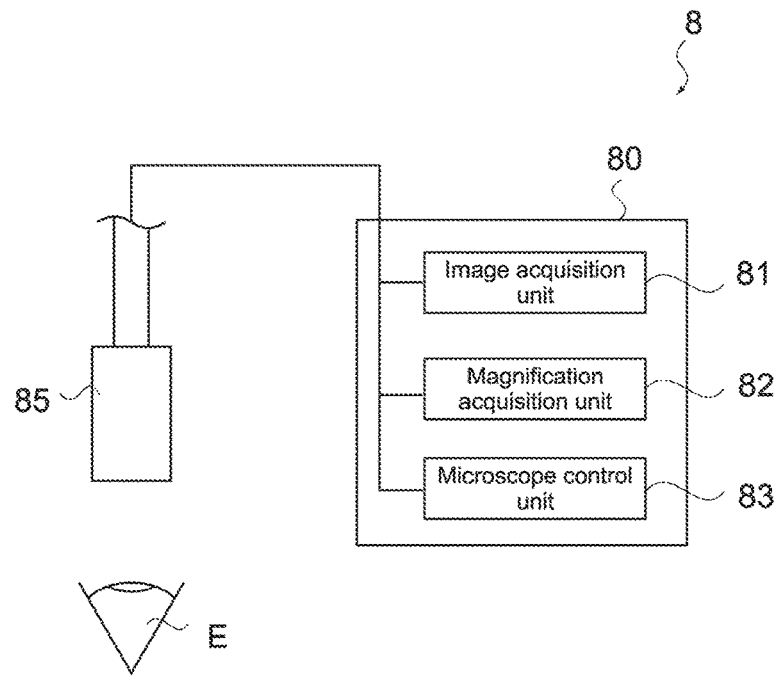
FIG. 38 A schematic diagram showing a configuration of a surgery microscope system according to an eighth embodiment of the present technology.

FIG. 38 is a block diagram showing a configuration of a surgery microscope system 8 according to this embodiment. As shown in the figure, the surgery microscope system 8 includes an information processing apparatus 80 and a surgery microscope 85.

The information processing apparatus 80 is an apparatus that is capable of performing information processing, such as a personal computer. The information processing apparatus 80 may be integrally formed with the surgery microscope 85, and may be an apparatus independent from the surgery microscope 85. The configuration of the information processing apparatus 80 will be described later.

As shown in FIG. 35, the surgery microscope 85 faces the eye E to be treated, and picks up a microscope magnified image of the eye E. The configuration of the surgery microscope 85 is not particularly limited as long as the surgery microscope 85 is capable of picking up an image of the eye E. The surgery microscope 85 is capable of optically or digitally changing the magnification of the image, or changing the magnification of the image also with a relative position (distance) between the surgery microscope 85 and the eye E.

[Configuration of Information Processing Apparatus]

As shown in FIG. 38, the information processing apparatus 80 includes an image acquisition unit 81, a magnification acquisition unit 82, and a microscope control unit 83.

The image acquisition unit 81 acquires an image including the eye E. The image acquisition unit 81 is capable of acquiring a reference image and a target image, similarly to the image acquisition unit 11 according to the first embodiment. The image acquisition unit 81 may acquire each image directly from the examination apparatus, the surgery microscope, or the like, and may acquire each image via a network or each image stored in storage. The image acquisition unit 81 supplies the acquired image to the magnification acquisition unit 82 and the microscope control unit 83.

The magnification acquisition unit 82 acquires the magnification between the reference image and the target image. The magnification acquisition unit 82 is capable of acquiring the magnification by using any one the methods described in the embodiments 1 to 4, i.e., at least one of object recognition processing on each image, the distance between the imaging apparatus and the eye to be treated, and the zoom factor of the imaging apparatus. The magnification acquisition unit 82 supplies the acquired magnification to the microscope control unit 83.

The microscope control unit 83 controls the surgery microscope 85 by using the magnification supplied from the magnification acquisition unit 82. The surgery microscope 85 in this embodiment may be a surgery microscope including a band-pass filter that can be introduced into an optical system. The microscope control unit 83 may be capable of switching the band-pass filter provided to the surgery microscope 85 depending on the magnification. Details thereof will be described later.

The information processing apparatus 80 has the configuration described above. Note that the above-mentioned respective images do not necessarily need to be picked up by the examination apparatus or the surgery microscope, and only have to include at least an eye to be treated. Furthermore, the above-mentioned respective images may be a still image or one frame of a moving image.

[Details of Microscope Control Unit]

As described above, the microscope control unit 83 controls the surgery microscope 85 depending on the magnification M.

Figure 39:
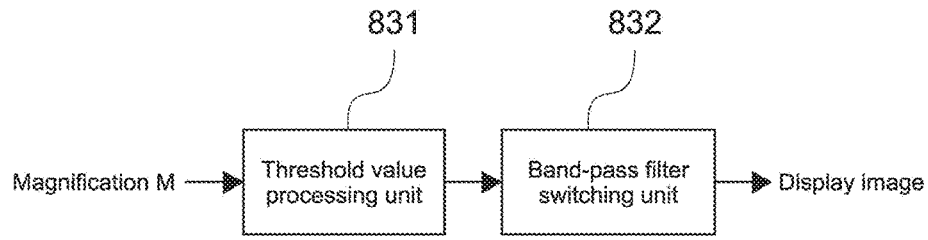
FIG. 39 A block diagram showing a configuration and operation of a microscope control unit of the surgery microscope system.

FIG. 39 is a block diagram showing a configuration and operation of the microscope control unit 83. As shown in the figure, the microscope control unit 83 includes a threshold value processing unit 831 and a band-pass filter switching unit 832.

When the magnification M is supplied to the threshold value processing unit 831, the threshold value processing unit 831 performs threshold value processing on the magnification M, and selects a kind of a band-pass filter. Examples of the kind of a band-pass filter include a red-pass filter and a green/blue-pass filter. The threshold value processing unit 831 may, for example, select a red-pass filter in the case where the magnification M is not less than a threshold value, and a green/blue-pass filter in the case where the magnification M is less than the threshold value. The threshold value processing unit 831 supplies the selected kind of a band-pass filter to the band-pass filter switching unit 832.

The band-pass filter switching unit 832 instructs the surgery microscope 85 to introduce the band-pass filter whose kind is supplied from the threshold value processing unit 831 into an optical system.

Figure 40:
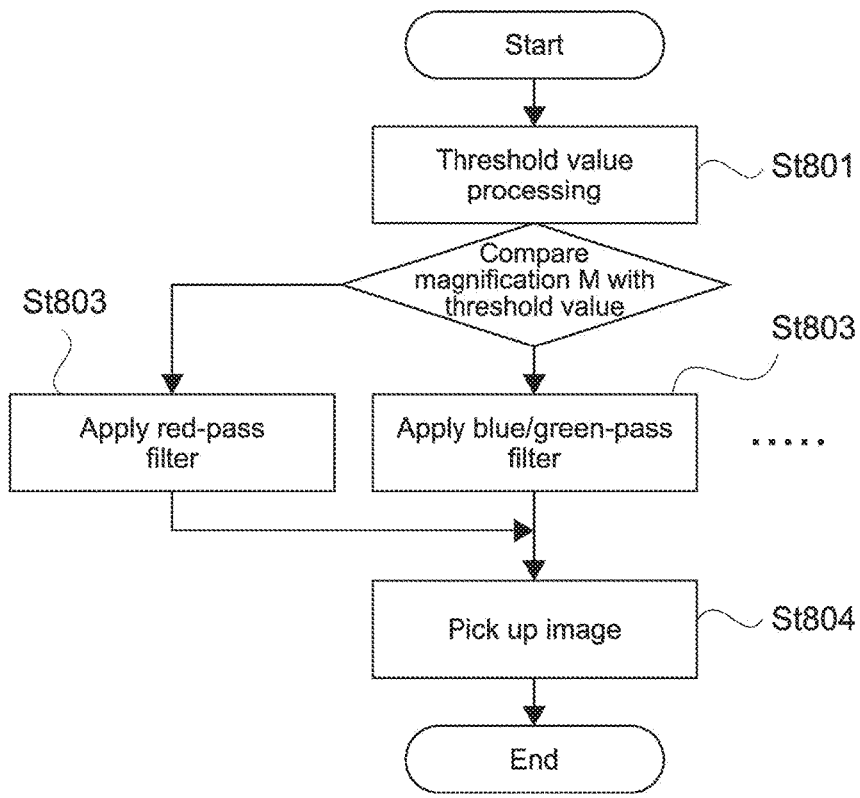
FIG. 40 A flowchart showing an operation of the microscope control unit of the surgery microscope system.

FIG. 40 is a flowchart showing an operation of the microscope control unit 83. As shown in the figure, when the magnification M is supplied to the threshold value processing unit 831, the threshold value processing unit 831 performs threshold value processing on the magnification M (St801). Specifically, the threshold value processing unit 631 selects a kind of a band-pass filter depending on the result of comparing the magnification M with a threshold value (St801), and give instructions to the band-pass filter switching unit 832. The band-pass filter switching unit 832 instructs the imaging apparatus to introduce the band-pass filter whose kind is supplied from the threshold value processing unit 831 into an optical system (St803). The surgery microscope 85 picks up an image of the eye E by using the introduced band-pass filter (St804).

As described above, the band-pass filter of the surgery microscope 85 is switched by the microscope control unit 83 depending on the magnification M, and an image of the eye E is picked up. The image acquisition unit 81 is capable of acquiring this image from the surgery microscope 85, and causing a display to display it. It is considered that when a user performs a zoom-in operation in which the magnification M is increased, the user intends to check the inside of a cornea in detail. In this regard, in order to improve the visibility inside the cornea, the microscope control unit 83 applies a band-pass filter that emphasizes the red color (band-pass filter through which the red color passes). Further, it is considered that when a user performs a zoom-out operation in which the magnification M is decreased, the user intends to check presence or absence of bleeding or the entire eye in the overhead view. In this regard, the microscope control unit 83 applies a band-pass filter that emphasizes the green or blue color (band-pass filter through which the green or blue color passes) in order to emphasize a blood vessel.

The microscope control unit 83 has the configuration described above. As described above, the microscope control unit 83 switches the kind of a band-pass filter in the optical system of the imaging apparatus depending on the magnification M. Because the switching of the band-pass filter is automatically selected depending on the magnification M, the user does not need to manually select it, and it is possible to provide high convenience.

Ninth Embodiment

A surgery microscope system according to a ninth embodiment of the present technology will be described.

[Configuration of Surgery Microscope System]

Figure 41:
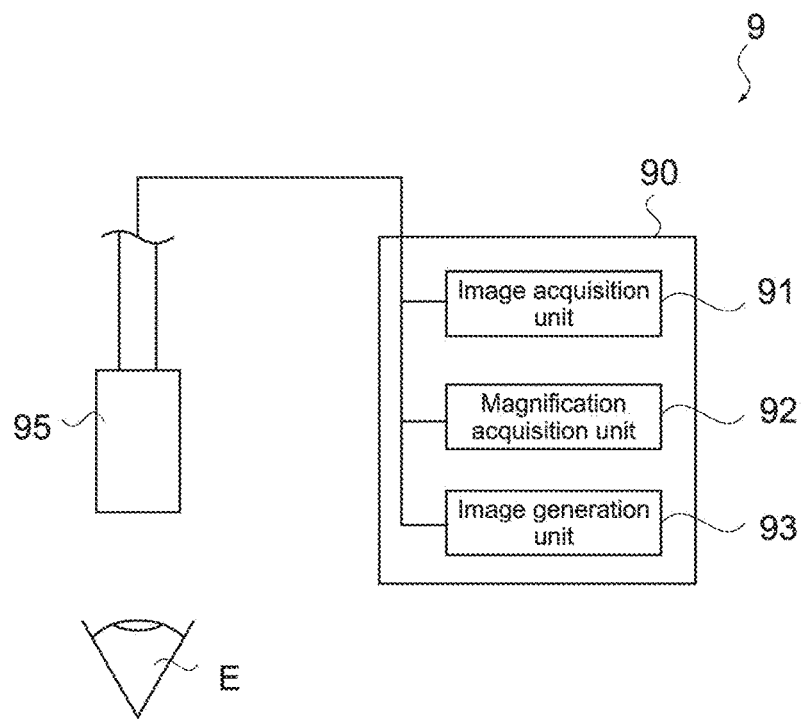
FIG. 41 A schematic diagram showing a configuration of a surgery microscope system according to a ninth embodiment of the present technology.

FIG. 41 is a block diagram showing a configuration of a surgery microscope system 9 according to this embodiment. As shown in the figure, the surgery microscope system 9 includes an information processing apparatus 90 and a surgery microscope 95.

The information processing apparatus 90 is an apparatus that is capable of performing information processing, such as a personal computer. The information processing apparatus 90 may be integrally formed with the surgery microscope 95, and may be an apparatus independent from the surgery microscope 95. The configuration of the information processing apparatus 90 will be described later.

As shown in FIG. 41, the surgery microscope 95 faces the eye E to be treated, and picks up a microscope magnified image of the eye E. The configuration of the surgery microscope 95 is not particularly limited as long as the surgery microscope 95 is capable of picking up an image of the eye E. The surgery microscope 95 is capable of optically or digitally changing the magnification of the image, or changing the magnification of the image also with a relative position (distance) between the surgery microscope 95 and the eye E.

(Configuration of Information Processing Apparatus)

As shown in FIG. 41, the information processing apparatus 90 includes an image acquisition unit 91, a magnification acquisition unit 92, and an image generation unit 93.

The image acquisition unit 91 acquires an image including the eye E. The image acquisition unit 91 is capable of acquiring a reference image and a target image, similarly to the image acquisition unit 11 according to the first embodiment. The image acquisition unit 91 may acquire each image directly from the examination apparatus, the surgery microscope, or the like, and may acquire each image via a network or each image stored in storage. The image acquisition unit 91 supplies the acquired image to the magnification acquisition unit 92 and the image generation unit 93.

The magnification acquisition unit 92 acquires the magnification between the reference image and the target image. The magnification acquisition unit 92 is capable of acquiring the magnification by using any one the methods described in the embodiments 1 to 4, i.e., at least one of object recognition processing on each image, the distance between the imaging apparatus and the eye to be treated, and the zoom factor of the imaging apparatus. The magnification acquisition unit 92 supplies the acquired magnification to the image generation unit 93.

The image generation unit 93 generates a navigation image that is a three-dimensional (3D) image by using the magnification supplied from the magnification acquisition unit 92. The surgery microscope 95 according to this embodiment may be a surgery microscope that is capable of picking up a 3D image. The image generation unit 93 is capable of adjusting a 3D parallax depending on the magnification. Details thereof will be described later.

The information processing apparatus 90 has the configuration described above. Note that the above-mentioned respective images do not necessarily need to be picked up by the examination apparatus or the surgery microscope, and only have to include at least an eye to be treated. Furthermore, the above-mentioned respective images may be a still image or one frame of a moving image.

[Details of Image Generation Unit]

As described above, the image generation unit 93 adjusts a parallax of a 3D image depending on the magnification M.

Figure 42:
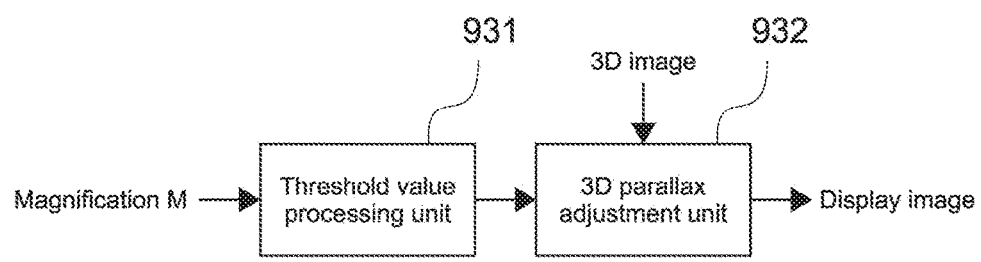
FIG. 42 A block diagram showing a configuration and operation of an image generation unit of the surgery microscope system.

FIG. 42 is a block diagram showing a configuration and operation of the image generation unit 93. As shown in the figure, the image generation unit 93 includes a threshold value processing unit 931 and a 3D parallax adjustment unit 932.

When the magnification M is supplied to the threshold value processing unit 931, the threshold value processing unit 931 performs threshold value processing on the magnification M, and selects the degree of emphasis of a parallax in a 3D image. The threshold value processing unit 931 may reduce the degree of emphasis of a parallax in the case where the magnification M is not less than a threshold value, and increase the degree of emphasis of a parallax in the case where the magnification M is less than the threshold value. Further, the threshold value processing unit 931 does not necessarily need to perform emphasis of a parallax in the case where the magnification M is not less than the threshold value. The threshold value processing unit 831 supplies the selected degree of emphasis of a parallax to the 3D parallax adjustment unit 932.

The 3D parallax adjustment unit 932 adjusts the parallax of the 3D image by the degree of emphasis supplied from the threshold value processing unit 931, and generates a 3D image.

Figure 43:
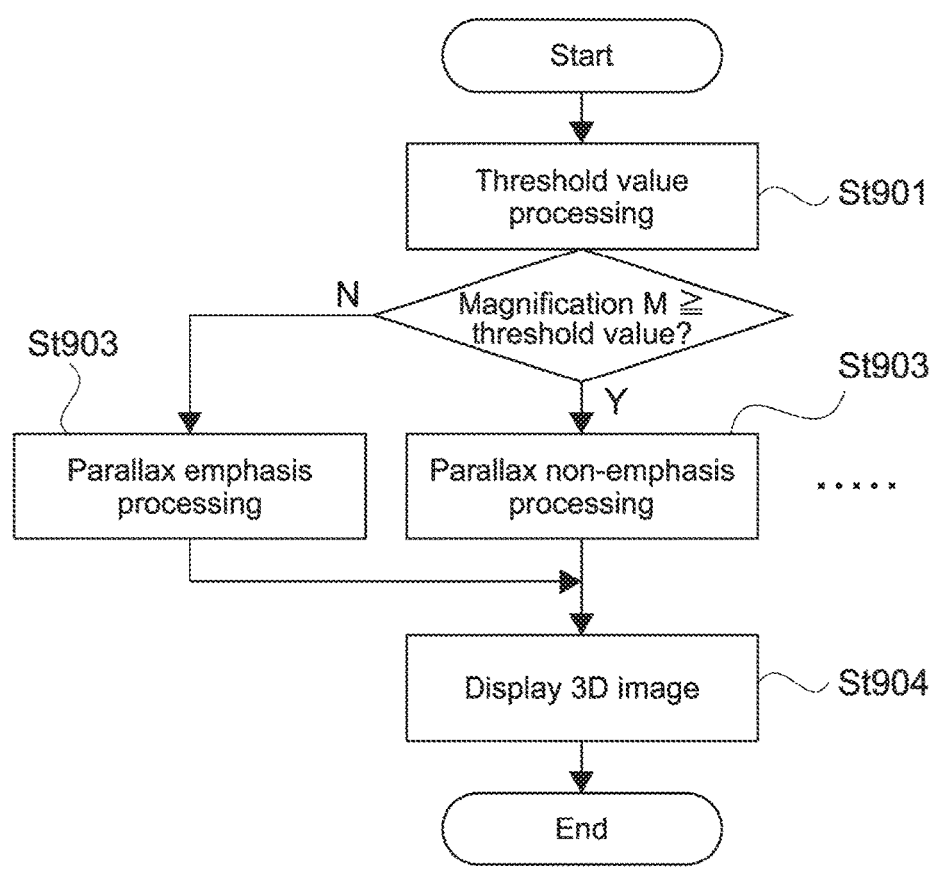
FIG. 43 A flowchart showing an operation of the image generation unit of the surgery microscope system.

FIG. 43 is a flowchart showing an operation of the image generation unit 93. As shown in the figure, when the magnification M is supplied to the threshold value processing unit 931, the threshold value processing unit 931 performs threshold value processing on the magnification M (St901). Specifically, the threshold value processing unit 931 selects the degree of emphasis of a parallax depending on the result of comparing the magnification M with a threshold value (St901), and gives instructions to the 3D parallax adjustment unit 932. The 3D parallax adjustment unit 932 generates a 3D image by the degree of emphasis of a parallax supplied from the threshold value processing unit 931 (St903), and causes a display to display it (St904).

As described above, a 3D image whose degree of emphasis of a parallax is different depending on the magnification M is generated by the image generation unit 93. The image generation unit 93 is capable of causing a display to display the generated 3D image. When a user performs a zoom-in operation in which the magnification is increased, a 3D image with a high parallax is displayed because the image is enlarged. In this regard, the image generation unit 93 performs processing of not emphasizing the parallax, and presents a 3D image that is easy on the eyes. Further, when a user performs a zoom-out operation in which the magnification is decreased, a 3D image with a low parallax is displayed because the image is contracted. In this regard, the image generation unit 93 performs processing of emphasizing the parallax, and presents a stereoscopic 3D image.

The image generation unit 93 has the configuration described above. As described above, the image generation unit 93 changes the degree of emphasis of a parallax of a 3D image depending on the magnification M. Because the change in the degree of emphasis of a parallax is automatically selected depending on the magnification M, the user does not need to manually select it, and it is possible to provide high convenience.

It should be noted that the present technology may take the following configurations.

(1)

An information processing apparatus, including:

a magnification acquisition unit that acquires a magnification of a target image with respect to a reference image, the reference image being an image of an eye to be treated, the target image being an image of the eye picked up at a time different from an imaging time of the reference image; and an image generation unit that generates a navigation image including navigation information for guiding treatment of the eye on the basis of the magnification acquired by the magnification acquisition unit.

(2)

The information processing apparatus according to (1) above, wherein the magnification acquisition unit acquires the magnification on the basis of a ratio between a size of an image of an object detected in the reference image and a size of an image of the object detected in the target image.

(3)

The information processing apparatus according to (1) or (2) above, in which the magnification acquisition unit acquires the magnification on the basis of a ratio between a distance between an imaging apparatus and the eye of a time when the reference image is picked up and a distance between the imaging apparatus and the eye of a time when the target image is picked up.

(4)

The information processing apparatus according to any one of (1) to (3) above, in which the magnification acquisition unit acquires the magnification on the basis of a ratio between a zoom factor of an imaging apparatus of a time when the reference image is picked up and a zoom factor of the imaging apparatus of a time when the target image is picked up.

(5)

The information processing apparatus according to any one of (1) to (4) above, in which the magnification acquisition unit acquires the magnification on the basis of a ratio between a distance between an imaging apparatus and the eye of a time when the reference image is picked up and a distance between the imaging apparatus and the eye of a time when the target image is picked up, and a ratio between a zoom factor of an imaging apparatus of the time when the reference image is picked up and a zoom factor of the imaging apparatus of the time when the target image is picked up.

(6)
The information processing apparatus according to any one of (1) to (5) above, in which
the image generation unit performs image matching of the reference image and the target image by using the magnification, and generates the navigation image by using a result of the image matching.

(7)
The information processing apparatus according to any one of (1) to (6) above, in which
the image generation unit includes a characteristic point detection unit that detects a characteristic point in each of the reference image and the target image, and
the characteristic point detection unit detects a characteristic point in the target image by using the magnification.

(8)
The information processing apparatus according to any one of (1) to (7) above, in which
the characteristic point detection unit includes a scale range determination unit and a DoG image generation unit, the scale range determination unit determining a scale range of a Gaussian filter for generating a smoothed image for each of the reference image and the target image, the DoG image generation unit generating a DoG image in a scale range determined by the scale range determination unit for each of the reference image and the target image, and
the scale range determination unit controls a scale range for the target image by the magnification.

(9)
The information processing apparatus according to any one of (1) to (8) above, in which
the image generation unit includes a characteristic point matching unit that matches characteristic points detected in the reference image and the target image, and
the characteristic point matching unit performs the matching by using the magnification.

(10)
The information processing apparatus according to any one of (1) to (9) above, in which
the characteristic point matching unit includes a characteristic point pair selection unit and a scale value comparison unit, characteristic point pair selection unit selecting a characteristic point pair, the characteristic point pair being a pair of characteristic points detected in the reference image and the target image, the scale value comparison unit determining whether or not the characteristic point pair is right by using a scale ratio of the characteristic point pair, and
the scale value comparison unit controls a scale ratio to be determined to be right by using the magnification.

(11)
The information processing apparatus according to any one of (1) to (10) above, in which
the image generation unit includes a characteristic point detection unit and a characteristic point matching unit, the characteristic point detection unit detecting a characteristic point in each of the reference image and the target image, the characteristic point matching unit matching characteristic points detected in the reference image and the target image,
the characteristic point detection unit detects a characteristic point in the target image by using the magnification, and
the characteristic point matching unit performs the matching by using the magnification.

(12)
The information processing apparatus according to any one of (1) to (11) above, in which
the image generation unit generates a navigation image including navigation information that is different depending on the magnification.

(13)
The information processing apparatus according to any one of (1) to (12) above, in which
the image generation unit generates a navigation image including first navigation information when the magnification is less than a threshold value, and a navigation image including second navigation information when the magnification is not less than the threshold value, the first navigation information including a scale arranged at predetermined intervals, the second navigation information including a scale arranged at intervals smaller than those of the first navigation information.

(14)
A surgery microscope system, including:
a surgery microscope that picks up an image of an eye to be treated; and
an information processing apparatus including
a magnification acquisition unit that acquires a magnification of a target image with respect to a reference image, the reference image being an image of the eye, the target image being an image of the eye picked up at a time different from an imaging time of the reference image, and
an image generation unit that generates a navigation image for guiding treatment of the eye on the basis of the magnification acquired by the magnification acquisition unit.

(15)
An information processing method, including:
acquiring, by a magnification acquisition unit, a magnification of a target image with respect to a reference image, the reference image being an image of an eye to be treated, the target image being an image of the eye picked up at a time different from an imaging time of the reference image; and
generating, by an image generation unit, a navigation image for guiding treatment of the eye on the basis of the magnification acquired by the magnification acquisition unit.

REFERENCE SIGNS LIST 1, 2, 3, 4, 5, 6, 7, 8, 9 surgery microscope system
10, 20, 30, 40, 50, 60, 70, 80, 90 information processing apparatus
15, 25, 35, 45, 55, 65, 75, 85, 95 surgery microscope
11, 21, 31, 41, 51, 61, 71, 81, 91 image acquisition unit
12, 22, 32, 42, 52 input acceptance unit
13, 23, 33, 43, 53, 62, 72, 82, 92 magnification acquisition unit
14, 24, 34, 44, 54, 63, 73, 93 image generation unit
83 microscope control unit
541 characteristic point detection unit
542 characteristic point matching unit
5411 DoG image generation unit 5412 DoG extreme value searching unit
5413 scale range determination unit
5421 characteristic amount calculation unit
5422 characteristic amount correlation value calculation unit
5423 characteristic point pair selection unit
5424 scale value comparison unit

The invention claimed is:

1. An information processing apparatus, comprising:
circuitry configured to:
  acquire a magnification of a target image with respect to a reference image, wherein
    the reference image is a first image of an eye captured at a first time, and
    the target image is a second image of the eye captured at a second time different from the first time;
  match the reference image and the target image to determine a result of the match, wherein the reference image and the target image are matched based on the magnification; and
  generate a first navigation image that includes first navigation information to guide treatment of the eye based on the result.

2. The information processing apparatus according to claim 1, wherein the circuitry is further configured to acquire the magnification based on a ratio between a size of an image of an object in the reference image and a size of an image of the object the target image.

3. The information processing apparatus according to claim 1, wherein the circuitry is further configured to acquire the magnification based on a ratio between a first distance between an imaging apparatus and the eye at the first time and a second distance between the imaging apparatus and the eye at the second time.

4. The information processing apparatus according to claim 1, wherein the circuitry is further configured to acquire the magnification based on a ratio between a first zoom factor of an imaging apparatus at the first time and a second zoom factor of the imaging apparatus at the second time.

5. The information processing apparatus according to claim 1, wherein the circuitry is further configured to acquire the magnification based on:
  a ratio between a first distance between an imaging apparatus and the eye at the first and a second distance between the imaging apparatus and the eye at the second time, and
  a ratio between a first zoom factor of the imaging apparatus at the first time and a second zoom factor of the imaging apparatus at the second time.

6. The information processing apparatus according to claim 1, wherein the circuitry is further configured to:
  detect a characteristic point in each of the reference image and the target image, and
  the characteristic point in the target image is detected based on the magnification.

7. The information processing apparatus according to claim 6, wherein
  the circuitry is further configured to:
  determine a scale range of a Gaussian filter to generate a smoothed image for each of the reference image and the target image;
  generate a difference of Gaussian (DoG) image in the scale range for each of the reference image and the target image; and
  control the scale range for the target image by the magnification.

8. The information processing apparatus according to claim 6, wherein
  the circuitry is further configured to match the characteristic point detected in the reference image and the characteristic point detected in the target image based on
  the magnification.

9. The information processing apparatus according to claim 8, wherein the circuitry is further configured to:
  select a characteristic point pair that is a pair of characteristic points detected in the reference image and the target image;
  determine that the characteristic point pair is right based on a scale ratio of the characteristic point pair; and
  control the scale ratio based on the magnification.

10. The information processing apparatus according to claim 1, wherein the circuitry is further configured to:
  detect a characteristic point in each of the reference image and the target image; and
  match the characteristic point detected in the reference image and the characteristic point detected in the target image, wherein
    the characteristic point in the target image is detected based on the magnification, and
    the characteristic point detected in the reference image is matched with the characteristic point detected in the target image based on the magnification.

11. The information processing apparatus according to claim 1, wherein
  the circuitry is further configured to generate a second navigation image that includes second navigation information based on the magnification, and
  the second navigation information is different the from the first navigation information.

12. The information processing apparatus according to claim 11, wherein the circuitry is further configured to:
  generate the first navigation image that includes the first navigation information based on the magnification that is less than a threshold value; and
  generate the second navigation image that includes the second navigation information based on the magnification is greater than or equal to the threshold value, wherein
    the first navigation information includes a first scale at a first plurality of intervals, and
    the second navigation information includes a second scale at a second plurality of intervals smaller than the first plurality of intervals.

13. A surgery microscope system, comprising:
  a surgery microscope configured to capture a reference image of an eye and a target image of the eye; and
  circuitry configured to:
  acquire a magnification of the target image with respect to the reference image, wherein
    the reference image is a first image of the eye captured at a first time,
    the target image is a second image of the eye captured at a second time different from the first time;
  match the reference image and the target image to determine a result of the match, wherein the reference image and the target image are matched based on the magnification; and
  generate a navigation image to guide treatment of the eye based on the result.

14. An information processing method, comprising:
in an information processing apparatus:

acquiring a magnification of a target image with respect to a reference image, wherein
  the reference image is a first image of an eye captured at a first time, and
  the target image is a second image of the eye captured at a second time different from the first time;
matching the reference image and the target image to determine a result of the match, wherein the reference image and the target image are matched based on the magnification; and
generating a navigation image to guide treatment of the eye based on the result.

* * * * *